US006514734B1

(12) United States Patent
Clapper et al.

(10) Patent No.: US 6,514,734 B1
(45) Date of Patent: *Feb. 4, 2003

(54) POLYBIFUNCTIONAL REAGENT HAVING A POLYMERIC BACKBONE AND LATENT REACTIVE MOIETIES AND BIOACTIVE GROUPS

(75) Inventors: David L. Clapper, Shorewood, MN (US); Melvin J. Swanson, Carver, MN (US); Sheau-Ping Hu, Falcon Heights, MN (US); Richard A. Amos, St. Anthony, MH (US); Terrence P. Everson, Eagan, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/591,564

(22) Filed: Jun. 9, 2000

Related U.S. Application Data

(63) Continuation of application No. 08/916,913, filed on Aug. 15, 1997, now Pat. No. 6,121,027.

(51) Int. Cl.$^7$ .......................... C12N 11/08; A61K 38/00; G01N 33/545; C07K 17/08
(52) U.S. Cl. ................. 435/180; 424/130.1; 424/184.1; 435/181; 435/395; 435/402; 436/531; 436/532; 514/2; 530/402; 530/815; 530/816
(58) Field of Search ................................. 435/180, 181, 435/395, 402; 424/130.1, 184.1; 436/531, 532; 514/2; 530/815, 816

(56) References Cited

U.S. PATENT DOCUMENTS

| | | | |
|---|---|---|---|
| 4,722,906 A | 2/1988 | Guire | 436/501 |
| 4,973,493 A | 11/1990 | Guire | 427/2 |
| 4,979,959 A | 12/1990 | Guire | 623/66 |
| 5,002,582 A | 3/1991 | Guire et al. | 623/66 |
| 5,217,492 A | 6/1993 | Guire et al. | 623/66 |
| 5,258,041 A | 11/1993 | Guire et al. | 623/66 |
| 5,263,992 A | 11/1993 | Guire | 623/66 |
| 5,563,056 A | 10/1996 | Swan et al. | 435/180 |
| 5,714,360 A | 2/1998 | Swan et al. | 435/174 |

FOREIGN PATENT DOCUMENTS

| | | |
|---|---|---|
| DE | 19533682 | 3/1997 |
| FR | 2655048 | 11/1989 |
| WO | WO9309176 | 5/1993 |
| WO | WO9316176 | 8/1993 |
| WO | WO9636653 | 11/1996 |

OTHER PUBLICATIONS

Hanker, J.S. and B.L. Giammara, "Biomaterials and Biomedical Devices", *Science* 242:885–892, 1988.
Kito, H.. et al., "Differentiated Biocompatible Design of Luminal and Outer Graft Surfaces", *ASAIO Journal* 39:M506–M511, 1993.
Clapper, D.L., et. al., "Photoimmobilized ECM Peptides Promote Cell Attachment and Growth on Biomaterials", *Trans. Soc. Biomat.* 16:42, 1993.
Cholakis, C.H. and M.V. Sefton, "In vitro platelet interactions with a heparin polyvinyl alcohol hydrogel", *J. Biomed. Mater. Res.* 23:399–415, 1989.
Cholakis, C.H., et. al., "Effect of heparin–PVA hydrogel on platelets in a chronic canine arterio–venous shunt", *J. Biomed. Mater. Res.* 23:417–441, 1989.
Kinoshita, Y., et. al., "Soft tissue reaction to collagen–immobilized porous polyethylene: subcutaneous implantation in rats for 20 wk", *Biomaterials* 14:209–215, 1993.
Alberts, B. et al., "Cell Adhesion, Cell Junctions, and the Extracellular Matrix", *Molecular Biology of the Cell*, 2nd ed., Garland Publ., Inc., New York (1989).
Kleinman, H.K, et.al., "The Laminins: A Family of Basement Membrane Glycoproteins Important in Cell Differentiation and Tumor Metastases", *Vitamins and Hormones* 47:161–186, 1993.
Hubbell, J.A., et. al., "Surface–grafted Cell–binding Peptides in Tissue Engineering of the Vascular Graft", *Ann. N.Y. Acad. Sci.* 665:253–258, 1992.
Mooradian, D.L., et. al., "Characterization of FN–C/H–V, a Novel Synthetic Peptide From Fibronectin That Promotes Rabbit Corneal Epithelial Cell Adhesion, Spreading, and Motility", *Invest. Ophth. & Vis. Sci.* 34:153–164, 1993.
Charonis, A.S., et. al., "A Novel Synthetic Peptide from the B1 Chain of Laminin with Heparin–binding and Cell Adhesion–promoting Activities", *J. Cell Biol.* 107: 1253–1260, 1988.
Koliakos, G.G, et. al., "The Binding of Heparin to Type IV Collagen: Domain Specificity with Identification of Peptide Sequences from the α2(IV) Which Preferentially Bind Heparin", *J. Biol. Chem.* 264:2313–2323, 1989.
Zazloff, M., "Antibiotic peptides as mediators of innate immunity", *Curr. Opinion Immunol.* 4:3–7, 1992.
Brzoska, J.B., et. al., "Silanization of Solid Substarates: A Step toward Reproducibility", *Langmuir* 10:4367–4373, 1994.
Grabar, K.C., et. al., "Preparation and Characterization of Au Colloid Monolayers", *Anal. Chem.* 67:735–743, 1995.
Matsuda, T. and T. Sugawara, "Development of surface photochemical modification method for micropatterning of cultured cells", *J. Biomed. Mater. Res.* 29:749–756 (1995).

(List continued on next page.)

*Primary Examiner*—David M. Naff
(74) *Attorney, Agent, or Firm*—Fredrikson & Byron, P.A.

(57) ABSTRACT

A polybifunctional reagent is provided having a polymeric backbone, one or more pendent latent reactive (preferably photoreactive) moieties, and two or more pendent bioactive groups. The reagent can be activated to form a bulk material or can be brought into contact with the surface of a previously formed biomaterial and activated to form a coating. The pendent bioactive groups function by promoting the attachment of specific molecules or cells to the bulk material or coated surface. Bioactive groups can include proteins, peptides, carbohydrates, nucleic acids and other molecules that are capable of binding noncovalently to specific and complimentary portions of molecules or cells.

220 Claims, No Drawings

OTHER PUBLICATIONS

McCarthy, J.B., et. al., "Localization and Chemical Synthesis of Fibronectin Peptides with Melanoma Adhesion and Heparin Binding Activities", *Biochem.* 27:1380–1388 (1988).

Worthington, C.C., Ed., "Worthington Enzyme Manual" (Worhtington Biochemical Corp., Freehold, NJ, 1977).

Imanishi et al., Block copolymerization of vinyl compounds by the terminal–group activation ofpoly($\alpha$–amino acids) and the characterization of block copolymers).

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 3 amino acid residues
      (B) TYPE: amino acid
      (C) STRANDEDNESS: single
      (D) TOPOLOGY: linear (xi) SEQUENCE DESCRIPTION: SEQ ID NO: 1:

Arg Gly Asp
1

(2) INFORMATION FOR SEQ ID NO: 2:

(i) SEQUENCE CHARACTERISTICS:
      (A) LENGTH: 4 amino acid residues
      (B) TYPE: amino acid
      (C) STRANDEDNESS: single
      (D) TOPOLOGY: linear (xi) SEQUENCE DESCRIPTION: SEQ ID NO: 2:

Arg Glu Asp Val
1

(2) INFORMATION FOR SEQ ID NO: 3:

(i) SEQUENCE CHARACTERISTICS:
      (A) LENGTH: 8 amino acid residues
      (B) TYPE: amino acid
      (C) STRANDEDNESS: single
      (D) TOPOLOGY: linear (xi) SEQUENCE DESCRIPTION: SEQ ID NO: 3:

Trp Gln Pro Pro Arg Ala Arg Ile
1             5

(2) INFORMATION FOR SEQ ID NO: 4:

(i) SEQUENCE CHARACTERISTICS:
        (A) LENGTH: 5 amino acid residues
        (B) TYPE: amino acid
        (C) STRANDEDNESS: single
        (D) TOPOLOGY: linear (xi) SEQUENCE DESCRIPTION: SEQ ID NO: 4:

```
Tyr Ile Gly Ser Arg
1               5
```

(2) INFORMATION FOR SEQ ID NO: 5:

(i) SEQUENCE CHARACTERISTICS:
        (A) LENGTH: 6 amino acid residues
        (B) TYPE: amino acid
        (C) STRANDEDNESS: single
        (D) TOPOLOGY: linear (xi) SEQUENCE DESCRIPTION: SEQ ID NO: 5:

```
Ser Ile Lys Val Ala Val
1               5
```

(2) INFORMATION FOR SEQ ID NO: 6:

(i) SEQUENCE CHARACTERISTICS:
        (A) LENGTH: 20 amino acid residues
        (B) TYPE: amino acid
        (C) STRANDEDNESS: single
        (D) TOPOLOGY: linear (xi) SEQUENCE DESCRIPTION: SEQ ID NO: 6:

```
Arg Tyr Val Val Leu Pro Arg Pro Val Cys Phe Glu Lys Gly Met
1               5                   10                  15
Asn Tyr Thr Val Arg
                20
```

(2) INFORMATION FOR SEQ ID NO: 7:

(i) SEQUENCE CHARACTERISTICS:
        (A) LENGTH: 13 amino acid residues
        (B) TYPE: amino acid
        (C) STRANDEDNESS: single
        (D) TOPOLOGY: linear (xi) SEQUENCE DESCRIPTION: SEQ ID NO: 7:

```
Gly Glu Phe Tyr Phe Asp Leu Arg Leu Lys Gly Asp Lys
1               5                   10
```

(2) INFORMATION FOR SEQ ID NO: 8:

(i) SEQUENCE CHARACTERISTICS:
        (A) LENGTH: 11 amino acid residues
        (B) TYPE: amino acid
        (C) STRANDEDNESS: single
        (D) TOPOLOGY: linear (xi) SEQUENCE DESCRIPTION: SEQ ID NO: 8:

```
Cys Lys Lys Gly Arg Gly Asp Ser Pro Ala Phe
1               5                   10
```

(2) INFORMATION FOR SEQ ID NO: 9:

(i) SEQUENCE CHARACTERISTICS:
        (A) LENGTH: 11 amino acid residues
        (B) TYPE: amino acid

```
            (C) STRANDEDNESS: single
            (D) TOPOLOGY: linear (xi) SEQUENCE DESCRIPTION: SEQ ID NO: 9:

Cys Lys Lys Trp Gln Pro Pro Arg Ala Arg Ile
1               5                   10

(2) INFORMATION FOR SEQ ID NO: 10:

(i) SEQUENCE CHARACTERISTICS:
            (A) LENGTH: 16 amino acid residues
            (B) TYPE: amino acid
            (C) STRANDEDNESS: single
            (D) TOPOLOGY: linear (xi) SEQUENCE DESCRIPTION: SEQ ID NO: 10:

Cys Lys Asn Asn Gln Lys Ser Glu Pro Leu Ile Gly Arg Lys Lys Thr
1               5                   10                  15

(2) INFORMATION FOR SEQ ID NO: 11:

(i) SEQUENCE CHARACTERISTICS:
            (A) LENGTH: 14 amino acid residues
            (B) TYPE: amino acid
            (C) STRANDEDNESS: single
            (D) TOPOLOGY: linear (xi) SEQUENCE DESCRIPTION: SEQ ID NO: 11:

Arg Tyr Val Val Leu Pro Arg Pro Val Cys Phe Glu Lys Lys
1               5                   10

(2) INFORMATION FOR SEQ ID NO: 12:

(i) SEQUENCE CHARACTERISTICS:
            (A) LENGTH: 15 amino acid residues
            (B) TYPE: amino acid
            (C) STRANDEDNESS: single
            (D) TOPOLOGY: linear (xi) SEQUENCE DESCRIPTION: SEQ ID NO: 12:

Cys Lys Gly Glu Phe Tyr Phe Asp Leu Arg Leu Lys Gly Asp Lys
1               5                   10                  15

(2) INFORMATION FOR SEQ ID NO: 13:

(i) SEQUENCE CHARACTERISTICS:
            (A) LENGTH: 9 amino acid residues
            (B) TYPE: amino acid
            (C) STRANDEDNESS: single
            (D) TOPOLOGY: linear (xi) SEQUENCE DESCRIPTION: SEQ ID NO: 13:

Gly Arg Gly Asp Ser Pro Lys Lys Cys
1               5

(2) INFORMATION FOR SEQ ID NO: 14:

(i) SEQUENCE CHARACTERISTICS:
            (A) LENGTH: 24 amino acid residues
            (B) TYPE: amino acid
            (C) STRANDEDNESS: single
            (D) TOPOLOGY: linear (xi) SEQUENCE DESCRIPTION: SEQ ID NO: 14:

Gly Ile Gly Lys Phe Leu His Ser Ala Lys Lys Phe Gly Lys Ala
1               5                   10                  15

Phe Val Gly Glu Ile Met Asn Ser Cys
```

-continued

```
16              20
```

(2) INFORMATION FOR SEQ ID NO: 15:

(i) SEQUENCE CHARACTERISTICS:
        (A) LENGTH: 40 bases
        (B) TYPE: nucleic acid
        (C) STRANDEDNESS: single
        (D) TOPOLOGY: linear (xi) SEQUENCE DESCRIPTION: SEQ ID NO: 15:

```
GTCTGAGTCG GAGCCAGGGC GGCCGCCAAC AGCAGGAGCA              40
```

(2) INFORMATION FOR SEQ ID NO: 16:

(i) SEQUENCE CHARACTERISTICS:
        (A) LENGTH: 50 bases
        (B) TYPE: nucleic acid
        (C) STRANDEDNESS: single
        (D) TOPOLOGY: linear (xi) SEQUENCE DESCRIPTION: SEQ ID NO: 16:

```
CCGTGCACGC TGCTCCTGCT GTTGGCGGCC GCCCTGGCTC CGACTCAGAC              50
```

POLYBIFUNCTIONAL REAGENT HAVING A POLYMERIC BACKBONE AND LATENT REACTIVE MOIETIES AND BIOACTIVE GROUPS

CROSS REFERENCE TO RELATED APPLICATIONS

The present application is a continuation of U.S. Ser. No. 08/916,913, filed Aug. 15, 1997, now U.S. Pat. No. 6,121,027, the entire disclosure of which is incorporated herein by reference.

FIELD OF THE INVENTION

In one aspect, this invention relates to reagents that can be used to modify biomaterial surfaces or to fabricate new biomaterials. In another aspect, the invention relates to biomaterials having surfaces that have been prepared or modified to provide desired bioactive function.

BACKGROUND OF THE INVENTION

Biomaterials have long been used to fabricate biomedical devices for use in both in vitro and in vivo applications. A variety of biomaterials can be used for the fabrication of such devices, including ceramics, metals, polymers, and combinations thereof. Historically, such biomaterials were considered suitable for use in fabricating biomedical devices if they provided a suitable combination of such basic properties as inertness, low toxicity, and the ability to be fabricated into desired devices. (Hanker, J. S. and B. L. Giammara, *Science* 242:885–892, 1988).

As the result of more recent advances, devices can now be provided with surfaces having various desirable characteristics, e.g., in order to better interface with surrounding tissue or solutions. For instance, approaches have been developed to promote the attachment of specific cells or molecules to device surfaces. A device surface, for instance, can be provided with a bioactive group that is capable of attracting and/or attaching to various molecules or cells. Examples of such bioactive groups include antigens for binding to antibodies, ligands for binding to cell surface receptors, and enzyme substrates for binding to enzymes.

Such bioactive groups have been provided on the surfaces of biomaterials in a variety of ways. In one approach, biomaterials can be fabricated from molecules that themselves present the desired bioactive groups on the surfaces of devices after fabrication. However, desirable bioactive groups are typically hydrophilic and cannot be incorporated into most metals or hydrophobic polymeric biomaterials at effective concentrations without disrupting the structural integrity of such biomaterials.

An alternative approach involves adding bioactive groups to the surfaces of biomaterials, e.g., after they have been fabricated into medical devices. Such bioactive groups can occasionally be added by adsorption. However, groups that have been added by adsorption cannot typically be retained on surfaces at high levels or for long periods of time.

The retention of such bioactive groups on a surface can be improved by covalent bonding of those groups to the surface. For instance, U.S. Pat. Nos. 4,722,906, 4,979,959, 4,973,493 and 5,263,992 relate to devices having biocompatible agents covalently bound via a photoreactive group and a chemical linking moiety to the biomaterial surface. U.S. Pat. Nos. 5,258,041 and 5,217,492 relate to the attachment of biomolecules to a surface through the use of long chain chemical spacers. U.S. Pat. Nos. 5,002,582 and 5,263,992 relate to the preparation and use of polymeric surfaces, wherein polymeric agents providing desirable properties are covalently bound via a photoreactive moiety to the surface. In particular, the polymers themselves exhibit the desired characteristics, and in the preferred embodiment, are substantially free of other (e.g., bioactive) groups.

Others have used photochemistry to modify the surfaces of biomedical devices, e.g., to coat vascular grafts. (See, e.g., Kito, H. et. al., *ASAIO Journal* 39:M506–M511, 1993. See also Clapper, D. L., et. al., *Trans. Soc. Biomat.* 16:42, 1993).

Cholakis and Sefton synthesized a polymer having a polyvinyl alcohol (PVA) backbone and heparin bioactive groups. The polymer was coupled to polyethylene tubing via nonlatent reactive chemistry, and the resultant surface was evaluated for thromboresistance in a series of in vitro and in vivo assays. For whatever reason, the heparin in the polymer prepared by Cholakis and Sefton did not provide effective activity. (Cholakis, C. H. and M. V. Sefton, *J. Biomed. Mater. Res.* 23:399–415, 1989. See also Cholakis, C. H., et. al., *J. Biomed. Mater. Res.* 23:417–441, 1989).

Finally, Kinoshita et. al. disclose the use of reactive chemistry to generate polyacrylic acid backbones on porous polyethylene, with collagen molecules being subsequently coupled to carboxyl moieties on the polyacrylic acid backbones. (See Kinoshita, Y., et. al., *Biomaterials* 14:209–215, 1993).

Generally, the resultant coating in the above-captioned situations is provided in the form of bioactive groups covalently coupled to biomaterial surfaces by means of short linear spacers. This approach works well with large molecular weight bioactive groups, such as collagen and fibronectin, where the use of short spacers is desired and the size of the bioactive group is quite large compared to that of the spacer itself.

The approaches described above, however, with the possible exception of Kinoshita et al., are not optimal for coating small molecular weight bioactive groups. Kinoshita does appear to coat small molecular weight molecules, although it describes a laborious multistep process that can detrimentally affect both yield and reproducibility.

Small molecular weight bioactive groups are typically provided in the form of either small regions derived from much larger molecules (e.g., cell attachment peptides derived from fibronectin) or as small molecules that normally diffuse freely to produce their effects (e.g., antibiotics or growth factors). It appears that short spacers can unduly limit the freedom of movement of such small bioactive groups, and in turn, impair their activity when immobilized. What are clearly needed are methods and compositions for providing improved concentrations of bioactive groups, and particularly small molecular weight groups, to a biomaterial surface in a manner that permits improved freedom of movement of the bioactive groups.

SUMMARY OF THE INVENTION

The present invention addresses the needs described above by providing a "polybifunctional" reagent comprising a polymeric backbone bearing one or more pendent photoreactive moieties and one or more, and preferably two or more, pendent bioactive groups. The reagent preferably includes a high molecular weight polymer backbone, preferably linear, having attached thereto an optimal density of both bioactive groups and photoreactive moieties. The reagent permits useful densities of bioactive groups to be coupled to a biomaterial surface, via one or more photoreactive groups. The backbone, in turn, provides a spacer function of sufficient length to provide the bioactive groups with greater freedom of movement than that which could otherwise be achieved, e.g., by the use of individual spacers (as described above).

As an added advantage, the present reagent permits the formation of inter- and intra-molecular covalent bonds within and/or between polymer backbones and the biomaterial surface, thereby providing an optimal and controllable combination of such properties as coating density, freedom of movement, tenacity and stability.

In addition to its use in modifying a biomaterial surface, a reagent of the invention provides other benefits as well. The photoreactive moieties allow individual polymer molecules to couple efficiently (e.g.,.crosslink) with adjacent polymer molecules. This crosslinking characteristic allows the polymers to generate thick coatings upon biomaterial surfaces and/or to generate independent films and bulk materials, either in vitro or in vivo.

The present invention also discloses a method for synthesizing a polybifunctional reagent and for providing a coated surface, such as the surface of a biomaterial, or biomedical device fabricated from such a biomaterial. The coated surface, having molecules of the polybifunctional reagent attached thereto in order to provide the device with desirable properties or attributes.

The photoreactive moieties can be activated in order to attach the polybifunctional reagent to a surface providing abstractable hydrogen atoms in such a manner that the pendent bioactive group(s) retain their desired bioactive function. Preferably, the reagent is attached to the surface in a "one step" method, that is, by applying a reagent to the surface and there activating one or more of its photoreactive groups in order to form a coating. In contrast, a "two step" method would involve a first step of immobilizing a polymeric backbone via photochemical means, and a second step of attaching (e.g., thermochemically) one or more bioactive groups to the immobilized backbone.

Preferred polybifunctional reagents of the invention can be used to coat the surfaces of existing biomaterials and/or to generate new biomaterials, e.g., by the formation of bulk materials. In either case, they can improve the surface properties of a biomedical device by providing covalently bound bioactive groups at the device surface. Preferred bioactive groups, in turn, act by either noncovalently binding to, or acting upon, specific complimentary portions of molecules or cells that come into contact with such groups.

In one preferred embodiment, a polybifunctional reagent of the invention is synthesized having a polymeric backbone, one or more photoreactive moieties, and two or more bioactive groups. The polymeric molecule of the invention is brought into contact with the surface of a previously formed biomaterial or into contact with another polymeric molecule of the invention. The photoreactive moieties are energized via an external stimulation to form, by means of active specie generation, a covalent bond between the reagent molecule and either the biomaterial surface or another reagent molecule. For instance, a biomaterial can be wetted in a solution containing a suitable reagent (typically for 0.1–5 minutes) and then exposed to light (typically for 0.1–2 minutes) to achieve covalent coupling.

Preferred bioactive groups function by promoting the attachment of specific molecules or cells to the surface. Preferred bioactive groups include, but are not limited to, proteins, peptides, carbohydrates, nucleic acids and other molecules that are capable of binding noncovalently to specific and complimentary portions of molecules or cells. Examples of such specific binding include cell surface receptors binding to ligands, antigens binding to antibodies, and enzyme substrates binding to enzymes. Preferably, the polymeric backbone comprises a synthetic polymeric backbone selected from the group consisting of addition type polymers, such as the vinyl polymers. More preferably, the photogroups each comprise a reversibly photoactivatable ketone.

DESCRIPTION OF THE PREFERRED EMBODIMENTS

As used herein, the following terms and words will have the following ascribed meanings:

"biomaterial" will refer to a material that is substantially insoluble in aqueous systems and that provides one or more surfaces for contact with fluids containing biological molecules, e.g., in vivo or in vitro aqueous systems containing tissues, cells, or biomolecules;

"device" will refer to a functional object fabricated from a biomaterial;

"coating", when used as a noun, will refer to one or more polymer layers on a biomaterial surface, and in particular, to one or more layers immobilized on a biomaterial surface by the activation of a polybifunctional reagent of the present invention;

"polybifunctional reagent", when used in the context of the presently claimed reagent, will refer to a molecule comprising a polymer backbone, to which are covalently bonded one or more photoreactive moieties and two or more bioactive groups;

"a photoreactive moiety" will refer to a chemical group that responds to a specific applied external energy source in order to undergo active specie generation, resulting in covalent bonding to an adjacent molecule or biomaterial surface;

"bioactive group" will refer to a molecule having a desired specific biological activity, such as a binding or enzymatic (catalytic) activity;

"polymer backbone" will refer to a natural polymer or a synthetic polymer, e.g., resulting from addition or condensation polymerization;

Preferred reagents of the invention comprise a synthetic polymer which serves as a backbone, one or more pendent photoreactive moieties which can be activated to provide covalent bonding to surfaces or adjacent polymer molecules, and two or more pendent low molecular weight biologically active moieties (bioactive groups).

Backbone. The polymer backbone can be either synthetic or naturally occurring, and is preferably a synthetic polymer selected from the group consisting of oligomers, homopolymers, and copolymers resulting from addition or condensation polymerization. Naturally occurring polymers, such as polysaccharides and polypeptides, can be used as well. Preferred backbones are biologically inert, in that they do not provide a biological function that is inconsistent with, or detrimental to, their use in the manner described.

Such polymer backbones can include acrylics such as those polymerized from hydroxyethyl acrylate, hydroxyethyl methacrylate, glyceryl acrylate, glyceryl methacrylate, acrylic acid, methacrylic acid, acrylamide and methacrylamide; vinyls such as polyvinyl pyrrolidone and polyvinyl alcohol; nylons such as polycaprolactam; derivatives of polylauryl lactam, polyhexamethylene adipamide and polyhexamethylene dodecanediamide, and polyurethanes; polyethers such as polyethylene oxide, polypropylene oxide, and polybutylene oxide; and biodegradable polymers such as polylactic acid, polyglycolic acid, polydioxanone, polyanhydrides, and polyorthoesters.

The polymeric backbone is chosen to provide a backbone capable of bearing one or more photoreactive moieties and two or more bioactive groups. The polymeric backbone is also selected to provide a spacer between the surface and the various photoreactive moieties and bioactive groups. In this manner, the reagent can be bonded to a surface or to an adjacent reagent molecule, to provide the bioactive groups with sufficient freedom of movement to demonstrate optimal activity. The polymer backbones are preferably water soluble, with polyacrylamide and polyvinylpyrrolidone being particularly preferred polymers.

Photoreactive moieties. Polybifunctional reagents of the invention carry one or more pendent latent reactive (preferably photoreactive) moieties covalently bonded to the polymer backbone. Photoreactive moieties are defined herein, and preferred moieties are sufficiently stable to be stored under conditions in which they retain such properties. See, e.g., U.S. Pat. No. 5,002,582, the disclosure of which is incorporated herein by reference. Latent reactive moieties can be chosen that are responsive to various portions of the electromagnetic spectrum, with those responsive to ultraviolet and visible portions of the spectrum (referred to herein as "photoreactive") being particularly preferred.

Photoreactive moieties respond to specific applied external stimuli to undergo active specie generation with resultant covalent boding to an adjacent chemical structure, e.g., as provided by the same or a different molecule. Photoreactive moieties are those groups of atoms in a molecule that retain their covalent bonds unchanged under conditions of storage but that, upon activation by an external energy source, form covalent bonds with other molecules.

The photoreactive moieties generate active species such as free radicals and particularly nitrenes, carbenes, and excited states of ketones upon absorption of external electric, electromagnetic or kinetic (thermal) energy. Photoreactive moieties may be chosen to be responsive to various portions of the electromagnetic spectrum, and photoreactive moieties that are responsive to e.g., ultraviolet and visible portions of the spectrum are preferred and are referred to herein occasionally as "photochemical" moiety.

Photoreactive aryl ketones are particularly preferred, such as acetophenone, benzophenone, anthraquinone, anthrone, and anthrone-like heterocycles (i.e., heterocyclic analogues of anthrone such as those having N, O, or S in the 10-position), or their substituted (e.g., ring substituted) derivatives. The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatable aryl ketones such as benzophenone and acetophenone are of particular importance inasmuch as these groups are subject to multiple reactivation in water and hence provide increased coating efficiency. Hence, photoreactive aryl ketones are particularly preferred.

The azides constitute a preferred class of latent reactive moieties and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive moieties and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive moieties include the aliphatic azo compounds such as azobisisobutyronitrile, the diazirines (—$CHN_2$) such as 3-trifluoromethyl-3-phenyldiazirine, the ketenes (—CH=C=O) such as ketene and diphenylketene.

Upon activation of the photoreactive moieties, the coating adhesion molecules are covalently bound to each other and/or to the material surface by covalent bonds through residues of the photoreactive groups. Exemplary photoreactive groups, and their residues upon activation, are shown as follows.

| Photoreactive Group | Residue Functionality |
| --- | --- |
| aryl azides | amine R—NH—R' |
| acyl azides | amide R—CO—NH—R' |
| azidoformates | carbamate R—O—CO—NH—R' |
| sulfonyl azides | sulfonamide R—$SO_2$—NH—R' |
| phosphoryl azides | phosphoramide $(RO)_2$PO—NH—R' |
| diazoalkanes | new C—C bond |
| diazoketones | new C—C bond and ketone |
| diazoacetates | new C—C bond and ester |
| beta-keto-alpha-diazoacetates | new C—C bond and beta-ketoester |
| aliphatic azo | new C—C bond |
| diazirines | new C—C bond |
| ketenes | new C—C bond |
| photoactivated ketones | new C—C bond and alcohol |

Bioactive Groups. Low molecular weight bioactive groups of the present invention are typically those that are intended to enhance or alter the function or performance of a particular biomedical device in a physiological environment. In a particularly preferred embodiment, the bioactive group is selected from the group consisting of cell attachment factors, growth factors, antithrombotic factors, binding receptors, ligands, enzymes, antibiotics, and nucleic acids. A reagent molecule of this invention includes at least one pendent bioactive group. The use of two or more pendent bioactive groups is presently preferred, however, since the presence of several such groups per reagent molecule tends to facilitate the use of such reagents.

Desirable cell attachment factors include attachment peptides (defined below), as well as large proteins or glycoproteins (typically 100–1000 kilodaltons in size) which in their native state can be firmly bound to a substrate or to an adjacent cell, bind to a specific cell surface receptor, and mechanically attach a cell to the substrate or to an adjacent cell. Naturally occurring attachment factors are primarily large molecular weight proteins, with molecular weights above 100,000 daltons.

Attachment factors bind to specific cell surface receptors, and mechanically attach cells to the substrate (referred to as "substrate adhesion molecules" herein) or to adjacent cells (referred to as "cell-cell adhesion molecules" herein) [Alberts, B. et. al., *Molecular Biology of the Cell*, 2nd ed., Garland Publ., Inc., New York (1989)]. In addition to promoting cell attachment, each type of attachment factor can promote other cell responses, including cell migration and differentiation. Suitable attachment factors for the present invention include substrate adhesion molecules such as the proteins laminin, fibronectin, collagens, vitronectin, tenascin, fibrinogen, thrombospondin, osteopontin, von Willibrand Factor, and bone sialoprotein. Other suitable attachment factors include cell-cell adhesion molecules ("cadherins") such as N-cadherin and P-cadherin.

Attachment factors useful in this invention typically comprise amino acid sequences or functional analogues thereof that possess the biological activity of a specific domain of a native attachment factor, with the attachment peptide typically being about 3 to about 20 amino acids in length. Native cell attachment factors typically have one or more domains that bind to cell surface receptors and produce the cell attachment, migration, and differentiation activities of the parent molecules. These domains consist of specific amino acid sequences, several of which have been synthesized and reported. to promote the attachment, spreading and/or proliferation of cells. These domains and functional analogues of these domains are termed "attachment peptides".

Examples of attachment peptides from fibronectin include, but are not limited to, RGD (Arg Gly Asp (Referred to herein as SEQ ID NO:1)) [Kleinman, H. K, et. al., *Vitamins and Hormones* 47:161–186, 1993], REDV (Arg Glu Asp Val (Referred to herein as SEQ ID NO:2)) [Hubbell, J. A., et. al., *Ann. N.Y. Acad. Sci.* 665:253–258, 1992], and C/H-V (WQPPRARI or Trp Gln Pro Pro Arg Ala Arg Ile (Referred to herein as SEQ ID NO:3)) [Mooradian, D. L., et. al., *Invest. Ophth. & Vis. Sci.* 34:153–164, 1993].

Examples of attachment peptides from laminin include, but are not limited to, YIGSR (Tyr-Ile-Gly-Ser-Arg (Referred to herein as SEQ ID NO:4)) and SIKVAV (Ser-Ile-Lys-Val-Ala-Val (Referred to herein as SEQ ID NO:5)) [Kleinman, H. K, et. al., *Vitamins and Hormones* 47:161–186, 1993] and F-9 (RYVVLPRPVCFEKGMNYTVR or (Arg-Tyr-Val-Val-Leu-Pro-Arg-Pro-Val-Cys-Phe-Glu-Lys-Gly-Met-Asn-Tyr-Thr-Val-Arg) (Referred to herein as SEQ ID NO:6)) [Charonis, A. S., et. al., *J. Cell Biol.* 107:1253–1260, 1988].

Examples of attachment peptides from type IV collagen include, but are not limited to, HEP-III (GEFYFDLRLKGDK or Gly-Glu-Phe-Tyr-Phe-Asp-Leu-Arg-Leu-Lys-Gly-Asp-Lys (Referred to herein as SEQ ID NO:7)) [Koliakos, G. G, et. al., *J. Biol. Chem.* 264:2313–2323, 1989]. Desirably, attachment peptides used in this invention have between about 3 and about 30 amino acid residues in their amino acid sequences. Preferably, attachment peptides have not more than about 15 amino acid residues in their amino acid sequences.

Other desirable bioactive groups present in the invention include growth factors, such as fibroblastic growth factors, epidermal growth factor, platelet-derived growth factors, transforming growth factors, vascular endothelial growth factor, bone morphogenic proteins and other bone growth factors, neural growth factors, and the like.

Yet other desirable bioactive groups present in the invention include antithrombotic agents that inhibit thrombus formation or accumulation on blood contacting devices. Desirable antithrombotic agents include heparin and hirudin (which inhibit clotting cascade proteins such as thrombin) as well as lysine. Other desirable antithrombotic agents include prostaglandins such as $PGI_2$, $PGE_1$, and $PGD_2$, which inhibit platelet adhesion and activation. Still other desirable antithrombotic agents include fibrinolytic enzymes such as streptokinase, urokinase, and plasminogen activator, which degrade fibrin clots. Another desirable bioactive group consists of lysine, which binds specifically to plasminogen, which in turn degrades fibrin clots.

Other desirable bioactive groups present in the invention include binding receptors, such as antibodies and antigens. Antibodies present on a biomaterial surface can bind to and remove specific antigens from aqueous media that comes into contact with the immobilized antibodies. Similarly, antigens present on a biomaterial surface can bind to and remove specific antibodies from aqueous media that comes into contact with the immobilized antigens.

Other desirable bioactive groups consist of receptors and their corresponding ligands. For example, avidin and streptavidin bind specifically to biotin, with avidin and streptavidin being receptors and biotin being a ligand. Similarly, fibroblastic growth factors and vascular endothelial growth factor bind with high affinity to heparin, and transforming growth factor beta and certain bone morphogenic proteins bind to type IV collagen. Also included are immunoglobulin specific binding proteins derived from bacterial sources, such as protein A and protein G, and synthetic analogues thereof Yet other desirable bioactive groups present in the invention include enzymes that can bind to and catalyze specific changes in substrate molecules present in aqueous media that comes into contact with the immobilized enzymes. Other desirable bioactive groups consist of nucleic acid sequences (e.g., DNA, RNA, and cDNA), which selectively bind complimentary nucleic acid sequences. Surfaces coated with specific nucleic acid sequences are used in diagnostic assays to identify the presence of complimentary nucleic acid sequences in test samples.

Still other desirable bioactive groups present in the invention include antibiotics that inhibit microbial growth on biomaterial surfaces. Certain desirable antibiotics may inhibit microbial growth by binding to specific components on bacteria. A particularly desirable class of antibiotics are the antibiotic peptides which seem to inhibit microbial growth by altering the permeability of the plasma membrane via mechanisms which, at least in part, may not involve specific complimentary ligand-receptor binding [Zazloff, M., *Curr. Opinion Immunol.* 4:3–7, 1992].

Biomaterials. Preferred biomaterials include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, styrene, vinyl chloride, vinyl acetate, vinyl pyrrolidone, and vinylidene difluoride. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetheretherketone.

Certain natural materials are also suitable biomaterials, including human tissue such as bone, cartilage, skin and teeth; and other organic materials such as wood, cellulose, compressed carbon, and rubber.

Other suitable biomaterials are composed of substances that do not possess abstractable hydrogens to which the photogroups can form covalent bonds. One such class of biomaterials can be made suitable for coating via photochemistry by applying a suitable primer coating which bonds to the biomaterial surface and provides a suitable substrate for binding by the photogroups. A subset of this group includes metals and ceramics which have oxide groups on their surfaces and are made suitable for coupling via photochemistry by adding a primer coating that binds to the oxide groups and provides abstractable hydrogens. The metals include, but are not limited to, titanium, stainless steel, and cobalt chromium. The ceramics include, but are not limited to, silicon nitride, silicon carbide, zirconia, and alumina, as well as glass, silica, and sapphire. One suitable class of primers for metals and ceramics consists of organosilane reagents, which bond to the oxide surface and provide hydrocarbon groups (Brzoska, J. B., et. al., *Langmuir* 10:4367–4373, 1994). The investigators have also discovered that —SiH groups are suitable alternatives for bonding of photogroups.

A second class of biomaterials that require an organic primer are the noble metals, which include gold, silver, copper, and platinum. Functional groups with high affinity to noble metals include —CN, —SH, and —$NH_2$, and organic reagents with these functional groups are used to apply organic monolayers onto such metals (Grabar, K. C., et. al., *Anal. Chem.* 67:735–743, 1995).

Another class of biomaterials that do not possess abstractable hydrogens are fibrous or porous. The invention polymers form covalently crosslinked polymer networks that fill the pores or form films around individual fibers and are therefore physically entrapped. Expanded polytetrafluoroethylene is such a biomaterial.

Biomaterials can be used to fabricate a number of devices capable of being coated with bioactive groups using a polybifunctional reagent of the present invention. Implant devices are one general class of suitable devices, and include, but are not limited to, vascular devices such as grafts, stents, catheters, valves, artificial hearts, and heart assist devices; orthopedic devices such as joint implants, fracture repair devices, and artificial tendons; dental devices such as dental implants and fracture repair devices; ophthalmic devices such as lenses and glaucoma drain shunts; and other catheters, synthetic prostheses and artificial organs. Other suitable biomedical devices include dialysis tubing and membranes, blood oxygenator tubing and membranes, blood bags, sutures, membranes, cell culture devices, chromatographic support materials, biosensors, and the like.

Preparation of Reagents. Those skilled in the art, given the present teaching, will appreciate the manner in which reagents of the present invention can be prepared using conventional techniques and materials. In one preferred method, a polymer backbone is prepared by the copolymerization of a base monomer, such as acrylamide or N-vinylpyrrolidone, with monomers having pendent photoreactive and/or thermochemically reactive groups. The polymers prepared by this copolymerization are then derivatized with the bioactive molecule by reaction through the thermochemically reactive groups. An example of such a coupling is the reaction between an N-oxysuccinimide (NOS) ester on the polymeric backbone with an amine group on the bioactive molecule.

An alternative preferred method involves the preparation of monomers that contain the desired bioactive group as well as a polymerizable function, such as a vinyl group. Such monomers can then be copolymerized with monomers containing photoreactive groups and with a base monomer such as acrylamide or N-vinylpyrrolidone.

A preferred procedure used to synthesize latent reactive peptide polymers involves the synthesis of N-substituted methacrylamide monomers containing each peptide (peptide monomer) and a methacrylamide monomer containing a substituted benzophenone (4-benzoylbenzoic acid, BBA). The peptide monomers were prepared by reacting the sulfhydryl moiety of each peptide with the maleimide moiety of N-[3-(6-maleimidylhexanamido)propyl]methacrylamide (Mal MAm). Then, each peptide monomer was copolymerized with acrylamide and the monomer containing BBA (BBA-APMA) to produce the final latent reactive peptide polymer.

Various parameters can be controlled to provide reagents having a desired ratio (whether on a molar or weight basis) of polymeric backbone, photoreactive moeities and bioactive groups. For instance, the backbone itself will typically provide between about 40 and about 400 carbon atoms per photoreactive group, and preferably between about 60 and about 300 carbon atoms.

With respect to the bioactive group, the length of the backbone can vary depending on such factors as the size of the bioactive group and the desired coating density. For instance, for relatively small bioactive groups (MW less than 3000) the polymeric backbone will typically be in the range of about 5 to about 200 carbon atoms per bioactive group, and preferably between about 10 and about 100. For larger bioactive groups, such as those having a molecular weight between about 3000 and about 50,000, the preferred backbone provides, on the average, between about 10 and about 5000 carbon atoms between bioactive group, and preferably between about 50 and 1000 carbon atoms. In each case, those skilled in the art, given the present description, will be able to determine the conditions suitable to provide an optimal combination of bioactive group density and freedom of movement.

Coating method. Reagents of the present invention can be coated onto biomaterial surfaces using techniques (e.g., dipping, spraying, brushing) within the skill of those in the relevant art. In a preferred embodiment, the polybifunctional reagent is first synthesized and then brought into contact (i.e., sufficient proximity to permit binding) with a previously formed biomaterial. The photoreactive group is energized via an external stimulation (e.g., exposure to a suitable light source) to form, via free active specie generation, a covalent bond between the reagent and either another polybifunctional reagent molecule or the biomaterial surface. This coating method is herein termed the "one step coating method", since photoreactive coupling chemistry attaches an invention polymer to a biomaterial surface, and no subsequent steps are required to add the bioactive group. The external stimulation that is employed desirably is electromagnetic radiation, and preferably is radiation in the ultraviolet, visible or infrared regions of the electromagnetic spectrum.

Photoactivatible polymers of the invention can also be used to immobilize biomoieties in patterns on the surfaces of biomaterials, for example using techniques previously described for generating patterns of coating with features of 50–350 $\mu$m in size. (See, Matsuda, T. and T. Sugawara, *J. Biomed. Mater. Res.* 29:749–756 (1995)). For example, hydrophilic patterns that inhibit the attachment and growth of endothelial cells can be generated by: 1) synthesizing latent reactive hydrophilic polymers, 2) adding the latent reactive polymers to tissue culture polystyrene plates, 3) illuminating the polymers through a pattern photomask, and 4) removing nonimmobilized polymers by washing with an appropriate solvent.

Such an approach can be employed with polymers of the present invention in order to immobilize patterns of specific biomoieties. For example, microarrays of specific binding molecules (e.g., antibodies, antigens/haptens, nucleic acid probes, etc.) can be immobilized on optical, electrochemical or semiconductor sensor surfaces to provide simultaneous multianalyte assay capabilities or multiple sensitivity range assays for single analytes. Patterned immobilization also provides a useful tool for developing a "laboratory on a chip," in which sequential processing/reaction steps occur along a fluid movement path in a multistep microvolume assay system. Patterning of cell attachment factors, for instance, those that promote the attachment of neural cells to electrodes, will permit the development of: 1) new generations of ultrasensitive biosensors and 2) artificial limbs that are directly controlled by the patient's nervous system.

Reagents of the invention can be covalently coupled to previously formed biomaterials to serve as surface coatings. The present reagent molecules can also be covalently coupled to adjacent molecules, in order to form films or bulk biomaterials. The surface coatings, films, and bulk biomaterials resulting from coupling via photoreactive moieties provide useful densities of bioactive groups on the surface of the resultant biomaterials.

Use of devices. Bioactive polymers of the present invention are used to modify the surfaces of existing biomaterials or to generate new biomaterials. Biomedical devices that contain the resultant biomaterials are used for a variety of in vitro and in vivo applications. For example, biomedical devices possessing cell attachment groups or growth factors as biomoieties promote the attachment and/or growth of cells on in vitro cell culture devices and improve tissue integration with implant devices such as vascular grafts, orthopedic implants, dental implants, cornea lenses, and breast implants. Biomedical devices possessing antithrombotic factors as biomoieties prevent thrombosis on the surfaces of blood contacting devices, such as catheters, heart valves, vascular stents, vascular grafts, stent grafts, artificial hearts, and blood oxygenators.

Biomedical devices such as resins or membranes possessing receptors or ligands as biomoieties can be used for affinity purification of a broad range of biomolecules. For example, heparin (which is also an antithrombotic moiety) is used to specifically bind and purify several clotting factors, protease inhibitors, lipoproteins, growth factors, lipolytic enzymes, extracellular matrix proteins and viral coat proteins. Staphylococcal Protein A specifically binds immunoglobulins and has proven to be very useful for purification of antibodies. Streptavidin is a protein that binds specifically to biotin with extremely high affinity. Streptavidin and biotin are a very useful pair of reagents as a secondary binding pair in diagnostic assays. Many times signal amplification, enhanced sensitivity and faster test performance can be achieved by using immobilized streptavidin.

Biomedical devices having surface-coated antibodies or antigens can be used in diagnostic tests that depend on the specificity of binding for sensitive detection of the complimentary antigen or antibody. The antibodies or antigens can be immobilized onto membranes, plastic tubes, microplate wells or solid state biosensor devices. Immobilized antibodies are also important for purification of a variety of biopharmaceutical agents. Proteins produced in bacteria or fungi by genetic engineering techniques can be purified by affinity purification with immobilized antibodies. Blood fractions, such as clotting factor VIII (antihemophiliac factor) are also purified by immobilized antibodies.

Biomedical devices having surfaces coated with nucleic acid sequences can be used to selectively bind complimentary nucleic acid sequences. Such devices are used in diagnostic assays to identify the presence of complimentary nucleic acid sequences in test samples. Devices having surface-coated enzymes as biomoieties can be used for a broad range of enzyme reactors, to catalyze either synthetic processes (e.g., making chiral pharmaceuticals) or degradative/conversion processes (e.g., degrading starch and converting glucose to fructose for making high fructose corn syrup).

Coated antimicrobial agents can be used to inhibit bacterial growth on the surfaces of devices. Such antimicrobial surfaces can reduce the rate of infections associated with implant devices, including several types of catheters (intravascular, peritoneal, hemodialysis, hydrocephalus, and urological), arteriovenous shunts, heart valves, vascular grafts, tracheotomy tubes, orthopedic and penile implants. Several in vitro devices can also benefit from such surfaces, e.g., by inhibiting biofilm formation. These include contact lens cases, dental unit water lines, plumbing used in food and pharmaceutical industries, food packaging, table tops and other surfaces used for food handling, and air filters.

EXAMPLES

The invention will be further described with reference to the following nonlimiting Examples. It will be apparent to those skilled in the art that many changes can be made in the embodiments described without departing from the scope of the present invention. Unless otherwise indicated, all percentages are by weight.

Example 1

Peptide Polymers

A. Synthesis of 4-Benzoylbenzoyl Chloride (BBA-Cl)

4-Benzoylbenzoic acid (BBA), 200.0 g (0.884 moles), was added to a dry 2 liter round bottom flask, followed by the addition of 273 ml of thionyl chloride. Dimethylformamide (DMF), 684 ul, was then added and the mixture was refluxed for 3–4 hours. After cooling, the excess thionyl chloride was removed on a rotary evaporator at water aspirator pressure. Any remaining thionyl chloride was removed by repeated evaporation with 3×100 ml of toluene. The final product was then recrystallized from 5:1 hexane:toluene with typical yields of BBA-Cl at >90% and a melting point of 92–94° C.

B. Synthesis of N-[3-(4-Benzoylbenzamido)propyl] methacrylamide (BBA-APMA)

N-(3-Aminopropyl)methacrylamide hydrochloride (APMA-HCl, 120 g, 0.672 moles), from Eastman Kodak Co., Rochester, N.Y.) were added to a dry 2 liter, three-neck round bottom flask equipped with an overhead stirrer. Phenothiazine, 23–25 mg, was added as an inhibitor, followed by 800 ml of chloroform. The suspension was cooled below 10° C. on an ice bath and 172.5 g (0.705 moles) of BBA-Cl were added as a solid. Triethylamine, 207 ml (1.485 moles), in 50 ml of chloroform was then added dropwise over a 1–1.5 hour time period. The ice bath was removed and stirring at ambient temperature was continued for 2.5 hours. The product was then washed with 600 ml of 0.3 N HCl and 2×300 ml of 0.07 N HCl. After drying over sodium sulfate, the chloroform was removed under reduced pressure and the product was recrystallized twice from 4:1 toluene:chloroform using 23–25 mg of phenothiazine in each recrystallization to prevent polymerization. Typical yields of BBA-APMA were 90% with a melting point of 147–151° C.

C. Synthesis of N-[3-(6-Maleimidohexanamido)propyl] methacrylamide (Mal-MAm)

6-Maleimidohexanoic acid was prepared by dissolving 6-aminohexanoic acid (100.0 g, 0.762 moles) in 300 ml of acetic acid in a three-neck, 3 liter flask equipped with an overhead stirrer and drying tube. Maleic anhydride, 78.5 g (0.801 moles), was dissolved in 200 ml of acetic acid and added to the 6-aminohexanoic acid solution. The mixture was stirred one hour while heating on a boiling water bath, resulting in the formation of a white solid. After cooling overnight at room temperature, the solid was collected by filtration and rinsed with 2×50 ml of hexane. Typical yield of the (Z)-4-oxo-5-aza-2-undecendioic acid was 90–95% with a melting point of 160–165° C.

(Z)-4-Oxo-5-aza-2-undecendioic acid, 150.0 g (0.654 moles), acetic anhydride, 68 ml (73.5 g, 0.721 moles), and phenothiazine, 500 mg, were added to a 2 liter three-neck round bottom flask equipped with an overhead stirrer. Triethylamine (TEA), 91 ml (0.653 moles), and 600 ml of tetrahydrofuran (THF) were added and the mixture was heated to reflux while stirring. After a total of 4 hours of reflux, the dark mixture was cooled to <60° C. and poured into a solution of 250 ml of 12 N HCl in 3 liters of water. The mixture was stirred 3 hours at room temperature and then was filtered through a filtration pad (Celite 545, J. T. Baker, Jackson, Tenn.) to remove solids. The filtrate was extracted with 4×500 ml of chloroform and the combined extracts were dried over sodium sulfate. After adding 15 mg of phenothiazine to prevent polymerization, the solvent was removed under reduced pressure. The 6-maleimidohexanoic acid was recrystallized from 2:1 hexane:chloroform to give typical yields of 55–60% with a melting point of 81–85° C.

The N-oxysuccinimide ester (NOS) of 6-maleimidohexanoic acid was prepared by dissolving 1.0 g (4.73 mmole) of 6-maleimidohexanoic acid and 0.572 g (4.97 mmole) of N-hydroxysuccinimide (NHS) in 10 ml of dry dioxane, followed by the addition of 1.074 g (5.21 mmole) of 1,3-dicyclohexylcarbodiimide (DCC). The reaction mixture was allowed to stir overnight at room temperature. The 1,3-dicyclohexylurea byproduct was removed by filtration and the filter cake was rinsed with 3×10 ml of dioxane. Phenothiazine (0.2 mg) was added and the solution was evaporated under reduced pressure. The resulting solid was extracted with hexane to remove any excess DCC and this product was used without any additional purification.

The N-succinimidyl 6-maleimidohexanoate, 414 mg (1.34 mmole), and N-(3-aminopropyl)methacrylamide hydrochloride, 200 mg (1.12 mmole), were diluted with 10 ml of chloroform, followed b the addition of 153 μl (1.10 mmole) of TEA over a 1 hour period at room temperature. The mixture was allowed to stir overnight at room temperature. The product was isolated by evaporation and purified by silica gel flash chromatography using a 99:1, followed by a 97:3 chloroform:methanol gradient. Pooling of fractions, addition of 10 mg p-methoxyphenol, and evaporation of solvent gave 261 mg of product. Mass spectral analysis of a sample gave M$^+$=335 (10.7%) and NMR showed maleimide (6.6 ppm) and allylic methyl (2.0 ppm) proton peaks.

D. Synthesis of Peptide Monomers

Five peptides were used as biomoieties. Each peptide moiety was synthesized by standard solid-phase synthesis methods and is identified below by its common name, a representative literature citation, the parent protein from which it was identified, and the specific sequence used (indicated by standard single letter notation for identifying amino acids).

| Common name | Literature citation | Parent protein | Sequence use |
|---|---|---|---|
| RGD | Kleinman, et al[1] | fibronectin | Cys Lys Lys Gly Arg Gly Asp Gly Asp Ser Pro Ala Phe (Referred to herein as SEQ ID NO:8) |
| C/H-V | Mooradian, et al[2] | fibronectin | Cys Lys Lys Trp Gln Pro Pro Arg Ala Arg Ile (Referred to herein as SEQ ID NO: 9) |
| C/H-II | McCarthy, et al[3] | fibronectin | Cys Lys Asn Asn Gln Lys Ser Glu Pro Leu Ile Gly Arg Lys Lys Thr (Referred to herein as SEQ ID NO: 10) |
| F-9 | Charonis, et al[4] | laminin | Arg Tyr Val Val Leu Pro Arg Pro Val Cys Phe Glu Lys Lys (Referred to herein as SEQ ID NO:11) |
| HEP-III | Koliakos, et al[5] | type IV collagen | Cys Lys Gly Glu Phe Try Phe Asp Leu Arg Leu Lys Gly Asp Lys (Referred to herein as SEQ ID NO: 12) |

[1]Kleinman, H.K, et. al., Vitamins and Hormones 47:161-186 (1993).
[2]Mooradian, D.L., et. al., Invest. Ophth. & Vis. Sci. 34:153-164 (1993).
[3]McCarthy, J.B., et. al., Biochem. 27:1380-1388 (1988).
[4]Charonis, A.S., et. al., J. Cell Biol. 107:1253-1260 (1988).
[5]Koliakos, G.G, et. al., J. Biol. Chem. 264:2313-2323 (1989).

For each peptide sequence, the portion of the sequence that is not underlined represents the native sequence that is present in the parent protein. The portion of the sequence that is underlined represents amino acids that were added to provide specific functional groups. The lysine residues (K) were added to provide primary amines (epsilon amino groups) that were used for radiolabelling via reductive methylation. Cysteine residues (C) were added to provide sulfhydryl groups that were used for coupling each peptide to maleimide groups present on monomers that were subsequently polymerized to produce the peptide polymers. C/H-II contained sufficient lysine residues in its native sequence and did not require the addition of additional lysine residues; similarly F-9 contained a cysteine residue as part of its native sequence and did not require the addition of an additional cysteine residue.

An appropriate quantity of Mal-MAm was removed from a stock solution of Mal-MAm in chloroform and was placed in a reaction vial, dried under nitrogen stream, and redissolved in dimethylsulfoxide (DMSO). An equal molar amount of each peptide was dissolved in degassed 50 mM acetate buffer (pH 5), added to the reaction vial, and the mixture was stirred for 60–90 minutes at room temperature.

| Peptide type | Mal-MAm (μmole) | DMSO (ml) | peptide (μmole) | acetate buffer (ml) | reaction time (min.) |
|---|---|---|---|---|---|
| RGD | 53.4 | 2 | 53.4 | 10 | 90 |
| F-9 | 40.4 | 1 | 40.4 | 7 | 60 |
| C/H-V | 8.6 | 0.2 | 8.6 | 1.3 | 90 |
| C/H-II | 38 | 2 | 38 | 10 | 90 |
| HEP-III | 6.4 | 0.3 | 6.4 | 2.7 | 90 |

E. Synthesis of Photoreactive Polyacrylamides Using Peptide Monomers (Peptide Polymers)

BBA-APMA was dissolved at a concentration of 10 mg/ml in DMSO, and acrylamide was dissolved at a concentration of 100 mg/ml in water. The peptide monomers were not purified after being synthesized and remained dissolved in solutions of acetate buffer containing DMSO as described above. The appropriate molar amounts of BBA-APMA monomer and acrylamide were then added to each reaction vial. Each mixture was degassed by water aspiration for 15 minutes. Ammonium persulfate (10% stock solution in water) and N,N,N',N'-tetramethylethylenediamine (TEMED) were added (in the amounts indicated below) to catalyze the polymerizations. Each mixture was degassed again and incubated overnight at room temperature in a sealed dessicator. Each resultant peptide copolymer was dialyzed against water (using Spectra/Por 50,000 MWCO dialysis tubing from Spectrum Medical Industries, Houston, Tex.) at 4° C. to remove unincorporated reactants and then lyophilized.

The following table indicates the amount of each reactant that was added for each copolymerization.

|  | RGD | F-9 | C/H-V | C/H-II | HEP-III |
|---|---|---|---|---|---|
| Peptide monomer ($\mu$mol) | 53.4 | 40.4 | 8.6 | 38.0 | 6.4 |
| BBA-APMA monomer ($\mu$mol) | 21.4 | 16.2 | 3.44 | 15.2 | 2.56 |
| Acrylamide ($\mu$mol) | 873 | 986 | 168 | 986 | 176 |
| 10% ammonium persulfate ($\mu$l) | 130 | 93 | 40 | 130 | 33 |
| TEMED ($\mu$l) | 26 | 19 | 8 | 26 | 6.6 |

The recovered amounts of each peptide polymer after lyophilization were 72 mg of RGD, 135 mg of F-9, 100 mg of C/H-II, 15.2 mg of C/H-V, and 17.8 mg of HEP-III.

F. Coupling of Peptide Polymers to Biomaterials

Three biomaterials were used: polystyrene (PS), polyurethane (PU), and silicone rubber (SR). Breakaway 96-well plate size polystyrene strips (Immulon I Removawell Strips, from Dynatech Laboratories, Inc., Chantilly, Va.) were used to determine the immobilized levels of each peptide polymer in radiolabelling experiments. Both 24- and 48-well PS culture plates (that were nonsterile and nonplasma treated) were obtained from Corning Costar Corp. (Cambridge, Mass.) and used for conducting the cell growth bioactivity assays. Flat PU sheets (Pellethane 55-D) and flat SR sheets were each obtained from Specialty Silicone Fabricators, Inc. (Paso Robles, Calif.) and punched to produce discs with diameters of 6, 10, and 15 mm diameters that respectively fit inside wells of 96, 48, and 24 well culture plates. The discs were used in both the radiolabelling assays and bioactivity assays.

Two different protocols were used to apply the peptides (peptide polymers or peptide reagent controls) to biomaterials, with the major difference being whether or not the peptides were dried onto the biomaterials before being illuminated to activate the latent reactive groups. With the dry immobilization protocol, the peptides were diluted in 50% (v/v) isopropanol (IPA) in water, added to biomaterials as indicated below, and dried before illumination. With the wet immobilization protocol, the peptides were diluted in water, added to biomaterials as indicated below, and not allowed to dry before illumination.

With each immobilization protocol, the final added concentration of peptide moieties was 50 $\mu$g/ml, and the following volumes were added per well of each type of culture plate: 50 $\mu$l/well of 96-well plates, 100 $\mu$l/well of 48-well plates, 200 $\mu$l/well of 24-well plates. As was indicate above, discs of PU and SR were placed in the bottoms of the plates for the coating and evaluation procedures.

The samples were illuminated with a Dymax lamp (model no. PC-2, Dymax Corporation, Torrington, Conn.) which contained a Heraeus bulb (W.C. Heraeus GmbH, Hanau, Federal Republic of Germany) to activate the photogroups present in each polymer, and produce covalent bonding to the biomaterial. The illumination duration was for 1–2 minutes at an intensity of 1–2 mW/cm$^2$ in the wavelength range of 330–340 nm. Adsorption controls were also generated with peptide polymers and peptide reagent controls that were not illuminated.

Following either photoimmobilization or adsorption, the peptide polymers and peptide reagent controls, respectively, were extensively washed on an orbital shaker (~150–200 rpm) to remove peptides that were not tenaciously bound to the substrate. The wash steps included: 1) an overnight wash with three changes in phosphate buffered saline (PBS), pH 7.3, containing 1% Tween 20 detergent, 2) a 30 minute wash/sterilization step in 70% (vol/vol) ethanol in water, and 3) four washes in sterile PBS.

G. Quantitation of Immobilized Levels of Peptides on Biomaterials

Two peptide polymers (RGD polymer and F-9 polymer) and their respective peptide reagent controls were radiolabelled with tritium by reductive methylation and used to determine the level of each peptide that was immobilized onto each biomaterial. The peptide reagent controls were not incorporated into polymers and consisted of RGD (sequence Gly Arg Gly Asp Ser Pro Lys Lys Cys (Referred to herein as SEQ ID NO: 13)) and F-9. The four tritium labeled peptides were respectively called, [$^3$H]-RGD polymer, [$^3$H]-F-9 polymer, [$^3$H]-RGD reagent control, and [$^3$H]-F-9 reagent control. Each tritium-labeled peptide was coated onto each biomaterial (PS breakaway strips, 6 mm discs of PU, or 6 mm discs of SR) using the dry immobilization protocol and the wash procedure described herein.

After the wash procedure, the PS break away strips were broken into individual wells, placed in scintillation vials (1 well/vial), dissolved in THF and counted in Aquasol-2 Fluor (DuPont NEN®, Boston, Mass.) to determine the dpm's/sample. The PU discs were swelled in THF and counted in Aquasol-2. The SR discs were dissolved in Soluene-350 Tissue Solubilizer and counted in Hionic Fluor (each from Packard Instrument Co., Meriden, Conn.). After the biomaterials were counted by liquid scintillation spectrometry, the final loading densities of each peptide (ng/cm$^2$) were calculated from the known specific activities (dpm/ng) of each tritiated reagent. A summary of the loading density results is given in the table below. Each value is the average of three or more determinations. Immobilized refers to illuminated samples. Adsorbed refers to nonilluminated samples. ND=not determined.

| Peptide | Biomaterial | Peptide Polymer Immobilized (ng/cm$^2$) | Peptide Polymer Adsorbed (ng/cm$^2$) | Peptide Reagent Control Adsorbed (ng/cm$^2$) |
|---|---|---|---|---|
| F-9 | PS | 2018 | 321 | 57 |
|  | SR | 1565 | 178 | 75 |
|  | PU | 139 | 90 | 31 |
| RGD | PS | 2575 | ND | 66 |
|  | SR | 1375 | 156 | 65 |
|  | PU | 562 | 109 | 23 |

In all cases, the immobilized peptide polymers (i.e., the polymer coatings which had been illuminated) exhibited the greatest loading densities. The loading densities of the peptide polymers were also biomaterial dependent, with the greatest retained levels of peptide polymers being on PS and SR, and the lowest retained levels being on PU. In each case, the retained levels of photoimmobilized peptide polymers were on the order of 1.5- to 9-fold greater than the adsorbed peptide polymers and on the order of 4.5- to 39-fold greater than the adsorbed peptide reagent controls.

H. Cell Attachment Activity of Immobilized Peptides

Calf pulmonary artery endothelial (CPAE) cells were purchased from ATCC (American Type Culture Collection, Rockville, Md.) and cultured as indicated by ATCC. The attachment assays were conducted in 48-well PS culture plates. When PU and SR were evaluated, discs of each material (with or without coatings) were placed in the bottoms of the culture plate wells. When PS was evaluated, the bottoms of the wells were coated. For each assay, uncoated and peptide coated biomaterials (PS, PU, and SR) were seeded at 50,000 cells per well in serum free media containing 2 mg/ml of bovine serum albumin (BSA fraction V, from Sigma Chemical Company, St. Louis, Mo.). The cells were allowed to attach to each biomaterial for two hours. Then the unattached cells were removed by aspiration, and the wells were rinsed twice with Hank's Balanced Salt Solution (Celox Corp., Hopkins, Minn.). Finally, the attached cells were quantitated by the addition of culture media containing a metabolic dye, MTT [3-(4,5-dimethylthiazol-2-yl)-2,5-diphenyltetrazolium bromide] which is converted from a yellow tetrazolium salt into an insoluble, purple formazan in the presence of viable cells. After a two hour incubation in culture media containing MTT, the media was removed, and the formazan dye that had been deposited inside the viable cells was solubilized (with acidic isopropanol) and read on a spectrophotometer at 570 nm. The absorbance of the formazan is directly proportional to the number of attached, viable cells present per well.

The following table summarizes results of cell attachment assays comparing immobilized peptide polymers and adsorbed peptide reagent controls. In each case, the relative numbers of cells that attached to the peptide-coated biomaterials (as determined by MTT dye) were divided by the number of cells that attached to the uncoated (UC) biomaterials to obtain a relative cell attachment score. Each value represents the average of 1 to 4 different experiments, with each experiment being conducted with 3 or 4 replicates. The peptides were immobilized onto PS using the wet immobilization protocol described herein and the peptides were immobilized onto SR and PU via the dry immobilization protocol. Immobil. Peptide Polymer refers to illuminated peptide polymer. Adsorbed Peptide Reagent refers to non-illuminated peptide reagent. ND=not determined.

|         | Polystyrene | | Silicone Rubber | | Polyurethane | |
|---------|---|---|---|---|---|---|
| Peptide | Im-mobil. Peptide Polymer | Ad-sorbed Peptide Reagent | Im-mobil. Peptide Polymer | Ad-sorbed Peptide Reagent | Im-mobil. Peptide Polymer | Ad-sorbed Peptide Reagent |
| RGD     | 10  | 1.4 | 6.2 | 1.1 | 4.3 | ND |
| F-9     | 5.7 | 0.8 | 0.9 | ND  | 1.9 | ND |
| C/H-V   | ND  | ND  | 1.3 | 0.4 | 1.4 | ND |

These results show that the photoimmobilized peptide polymers enhanced cell attachment to all three biomaterials. The greatest improvements were observed with RGD polymer photoimmobilized onto all three biomaterials and F-9 polymer photoimmobilized onto PS (4.3 to 10 fold improvements), with lesser improvements observed with F-9 polymer on PU and C/H-V polymer on SR and PU (1.3 to 1.9 fold improvements). In each case where adsorbed peptide reagent controls were compared to photoimmobilized peptide polymers, cell attachment was greater on the peptide polymers.

I. Cell Growth Activity of Immobilized Peptides

The growth assays were conducted in 24-well PS culture plates. When PU and SR were evaluated, discs of each material (with or without coatings) were placed in the bottoms of the culture plate wells. When PS was evaluated, the bottoms of the wells were coated. For each assay, uncoated and peptide coated biomaterials (PS, PU, and SR) were seeded with CPAE cells at 1500 cells per well and allowed to proliferate in vitro for 4 to 7 days. Then, the media was aspirated and the cell growth was quantitated using MTT dye.

The following table summarizes results that compared cell growth on uncoated substrates, adsorbed peptides, and peptide polymers. As with the attachment assays, the relative numbers of cells growing on each peptide coated biomaterial was divided by the number of cells growing on the uncoated (UC) biomaterials to obtain a relative cell growth score. Each value represents the average of 1 to 4 different experiments, with each experiment being conducted with 3 or 4 replicates. The dry immobilization protocol described herein was used to immobilize all peptides evaluated. Immobil. Peptide Polymer refers to illuminated peptide polymer. Adsorbed Peptide Reagent refers to non illuminated peptide reagent. ND=not determined.

|         | Polystyrene | | Silicone Rubber | | Polyurethane | |
|---------|---|---|---|---|---|---|
| Peptide | Im-mobil. Peptide Polymer | Ad-sorbed Peptide Reagent | Im-mobil. Peptide Polymer | Ad-sorbed Peptide Reagent | Im-mobil. Peptide Polymer | Ad-sorbed Peptide Reagent |
| RGD     | 17.5 | 1.2 | 1.7 | 1.1 | 9.4 | 1.7 |
| F-9     | 14.8 | 1.0 | 2.4 | 1.7 | 7.7 | 1.7 |
| C/H-V   | 11.3 | 1.0 | 1.0 | 2.0 | 3.9 | 0.7 |

In addition to the peptides shown in the table above, C/H-II and HEP-III were also evaluated for growth on PS. With these two peptides, growth on adsorbed peptides was 1.0 and 1.1 times that observed on uncoated PS, and growth on peptide polymers was 10.5 and 13 times that observed on uncoated PS. These two peptides (polymers and reagent controls) were immobilized via the wet immobilization protocol. The results with C/H-II and HEP-III are the averages of 1 and 2 experiments, respectively, with each experiment being conducted with 4 replicates.

These growth assays show that all five peptide polymers photoimmobilized onto PS promoted growth that was 10.5 to 17.5 fold greater than growth on uncoated PS. Also, the three peptide polymers enhanced cell growth on PU by 3.9 to 9.4 fold. Only slight improvements in cell growth were observed on SR.

Example 2

Hirudin Polymer

A. Synthesis of N-Succinimidyl 6-(4-Benzoylbenzamido) hexanoate (BBA-EAC-NOS)

BBA-Cl (30.00 g, 0.123 moles), prepared as described in Example 1, was dissolved in 450 ml of toluene. An amount (16.1 g, 0.123 moles) of 6-aminohexanoic acid (which will be alternatively referred to herein as C-aminocaproic acid, or as its abbreviated form EAC) was dissolved in 375 ml of 1

N NaOH and this solution was added to the solution of the acid chloride. The mixture was stirred vigorously to generate an emulsion for 45 minutes at room temperature. The product was then acidified with 1 N HCl and extracted with 3×450 ml of ethyl acetate. The combined extracts were dried over magnesium sulfate, filtered, and evaporated under reduced pressure. The 6-(4-benzoylbenzamido)hexanoic acid was recrystallized from toluene:ethyl acetate to give 36.65 g of product, m.p. 106–109° C.

The 6-(4-benzoylbenzamido)hexanoic acid (25 g, 73.7 mmoles), was added to a dry flask and dissolved in 500 ml of dry 1,4-dioxane. NHS (15.5 g, 0.135 moles) was added and the flask was cooled on an ice bath under a dry $N_2$ atmosphere. DCC (27.81 g, 0.135 moles), in 15 ml of 1,4-dioxane was then added and the mixture was stirred overnight. After filtration to remove the 1,3-dicyclohexylurea, the solvent was removed under reduced pressure and the product was recrystallized twice from ethanol to give 23.65 g of a white solid, m.p. 121–123° C.

B. Synthesis of a Photoreactive Polyacrylamide Containing Hirudin Ligands (Hirudin Polymer)

Methacryloyl-EAC-BBA was prepared by reacting 112 mg (0.629 mmole) of APMA-HCl, 358 mg (0.818 mmole) BBA-EAC-NOS and 80 mg (104 µl, 0.692 mmole) TEMED in 22 ml DMSO. The mixture was stirred for 4.5 hours. Then the NOS polymer was prepared by adding to this mixture 4.20 gm (59.1 mmole) acrylamide, 532 mg (3.15 mmole) N-acryloxysuccinimide (Eastman Kodak, Rochester, N.Y.) and 64 mg (0.39 mmole) of 2,2'-azobisisobutyronitrile (AIBN). The mixture was sparged with helium and incubated at 50° C. overnight. A portion of the resulting polymer solution (10 ml) was diluted with 10 ml DMSO and slowly added to vigorously stirred acetone (200 ml) to precipitate the polymer. The polymer was collected, washed with acetone to remove impurities, and dried under vacuum. A total of 1.47 g was recovered.

Recombinant hirudin with a purity of greater than 90% and an activity of 16,500±2000 ATU/mg was obtained from Transgene Laboratories (Strasbourg, France). (See below for definition of ATU.) Hirudin is an antithrombotic agent that acts by binding to and inhibiting the proteolytic activity of thrombin. Hirudin (10.5 mg, 1.52 µmole) was dissolved in 1 ml of 0.1 M carbonate buffer. The NOS polymer (prepared. as described above) was dissolved in DMSO at 4 mg/ml. Then 2 mg of the NOS polymer was added to the hirudin solution and mixed overnight. Half of the reaction mixture was dialyzed in a Spectra/Por 50,000 MWCO tubing against water, followed by lyophilization. A total of 5.9 mg of hirudin polymer was recovered, which contained 5.0 mg hirudin and 0.2 mole BBA per mole of hirudin. The hirudin was quantitated with a BCA protein assay kit (from Pierce Chemical Company, Rockford, Ill.) and the BBA content was determined spectrophotometrically.

A control polymer ("ethanolamine polymer") was prepared by adding ethanolamine instead of hirudin to the NOS polymer. The resultant ethanolamine polymer is uncharged and was used as a control in experiments that compared the binding of thrombin to a similar polymer that contained ethanolamine instead of hirudin.

C. Assay for Activities of Hirudin and Hirudin Polymer In Solution

The specific activities of hirudin and hirudin polymer were determined by standard protocols provided by Transgene and are expressed as antithrombin units (ATU's) per mg of hirudin. One ATU is the amount of hirudin that is required to inhibit the proteolytic activity of one NIH unit of thrombin. For these assays, a known amount of bovine thrombin (175–350 NIH units/mg., from Sigma Chemical Co., St. Louis, Mo.) was preincubated with a series of dilutions of hirudin or hirudin polymer, and the remaining thrombin activity was determined with a chromogenic substrate, Chromozym TH (from Boehringer Mannheim Corp, Indianapolis, Ind.). The specific activities of hirudin assayed before and after incorporation into the hirudin polymer were 11,710 and 10,204 ATU/mg, respectively. Therefore incorporation of hirudin into the polymer produced only a 13% decrease in its activity.

D. Coupling of Hirudin Polymer and Ethanolamine Polymer to Biomaterials.

Flat sheets of three biomaterials were used: 1) polyethylene (PE, primary reference material from the National Institutes of Health, Bethesda, Md.), 2) SR (medical grade SILASTIC® from Dow Corning Corporation, Midland, Mich.), and 3) PU (Tecoflex® from ThermoCardiosystems, Woburn, Mass.). Samples of each biomaterial were cut into either 6 mm diameter disks or 1×1 cm squares. To remove surface contaminants prior to coatings, the PU and PE samples were washed by brief immersion in IPA and SR was extracted 1 hour with hexane and dried overnight. In addition, the SR samples were treated with an argon plasma (3 min., 250 watts, 250 mtorr) just prior to application of the hirudin polymer or ethanolamine polymer.

The hirudin polymer was diluted to 1–25 µg/ml in 75:25 (v/v) water:IPA and added to one side of each biomaterial sample that was washed or extracted as described above. The added hirudin polymer solutions were allowed to dry and were then illuminated with a Dymax lamp. To remove loosely adherent hirudin polymer that remained after the coating procedures, each sample was washed 3 times for 15 minutes and then overnight in a 1% solution to Tween 20 in PBS. Then the Tween 20 was removed by rinsing the samples in deionized water.

Three types of control samples were also prepared: 1) uncoated controls to which hirudin polymer was not added, 2) samples to which the hirudin polymer was added but not illuminated, and 3) SR samples that were coated with the ethanolamine polymer. For the latter control, the ethanolamine polymer (prepared as described herein) was diluted in deionized water to 1 or 5 µg/200 µl. Then, 200 µl aliquots of each stock solution were added to one side of 1 $cm^2$ samples of SR, allowed to dry, photoactivated, and washed in Tween 20/PBS and deionized water as described herein for the hirudin polymer.

E. Quantitation of Hirudin Loading on Biomaterials.

Hirudin was radiolabeled via reductive methylation, incorporated into a hirudin polymer as described herein, and used to quantitate the amount of hirudin polymer that was immobilized onto each of three biomaterials as described herein. To count the retained tritium, the samples were dissolved in THF, diluted into Aquasol, and counted in a Packard 1900CA liquid scintillation counter. The results presented in the table below show that the amount of retained hirudin polymer was proportional to the amount added, and the amount retained after photoactivation is 2.3 to 66 times that retained without photoactivation. Each result is the average of 4 determinations. N.A.=not assayed.

|  | Added hirudin | Retained hirudin polymer | |
|---|---|---|---|
|  | polymer | without photoactivation | after photoactivation |
| Biomaterial | μg/cm² | μg/cm² | μg/cm² |
| PE | 1.0 | 0.0003 | 0.020 |
| PE | 5.0 | N.A. | 0.10 |
| PE | 25 | N.A. | 0.15 |
| PU | 1.0 | 0.027 | 0.062 |
| PU | 5.0 | N.A. | 0.114 |
| PU | 25 | N.A. | 0.312 |
| SR | 1.0 | N.A. | 0.019 |
| SR | 5.0 | N.A. | 0.043 |

F. Assay for Activity of Hirudin Polymer Coatings on Biomaterials.

Hirudin polymer that had not been labeled with tritium was coated onto each biomaterial as described herein. The activity of the immobilized hirudin polymer was then assayed by quantitating the binding of added tritium labeled thrombin ($^3$H-Thr). The $^3$H-Thr was prepared by labeling human thrombin (4000 NIH units/mg protein, from Sigma Chemical Co.) via reductive methylation. Each coated sample was incubated in a solution of 2 μg/ml of $^3$H-Thr in a Tris buffer (0.05 M Tris-HCl, 0.1 M NaCl, 0.1% PEG 3350, pH 8.5) for one hour and rinsed with the same buffer containing no thrombin to remove unbound thrombin. The samples were then dissolved THF, diluted in Aquasol and counted.

The results presented in the table below show that the amount of thrombin that was retained by hirudin-coated biomaterials was proportional to the amount of immobilized hirudin. Each result is the average of 4 determinations. SR+EP[1] and SR+EP[5] indicate SR samples that were coated with the ethanolamine polymer added at 1.0 and 5 μg/cm², respectively. N.A. equals not assayed. Control experiments were conducted in which thrombin was added to uncoated biomaterials, and the amounts of thrombin that bound to uncoated PE, PU, and SR were 0.01, 0.012, and 0.006 μg/cm², respectively. Comparisons of thrombin binding to uncoated PE and PU versus the same biomaterials coated with 25 μg/cm² of hirudin polymer show that the latter promoted 200 and 23 fold greater thrombin binding, respectively. Finally, the results with SR coated with the ethanolamine polymer show that the hirudin moiety is essential for binding thrombin.

| Biomaterial | Added hirudin polymer (μg/cm²) | Bound thrombin (μg/cm²) |
|---|---|---|
| PE | 0 | N.A. |
| PE | 1.0 | 0.020 |
| PE | 5.0 | 0.014 |
| PE | 25 | 0.200 |
| PU | 0 | N.A. |
| PU | 1.0 | 0.028 |
| PU | 5.0 | 0.137 |
| PU | 25 | 0.280 |
| SR | 0 | N.A. |
| SR | 1.0 | 0.004 |
| SR | 5.0 | 0.047 |
| SR + EP[1] | 0 | 0.004 |
| SR + EP[5] | 0 | 0.005 |

Example 3

Heparin Polymer

A. Synthesis of N-Succinimidyl 6-Maleimidohexanoate.

6-Maleimidohexanoic acid, 20.0 g (94.7 mmol) was dissolved in 100 ml of chloroform, followed by the addition of 60.1 g (0.473 mol) of oxalyl chloride. The resulting solution was then stirred for 2 hours at room temperature. The excess oxalyl chloride was removed under reduced pressure and the resulting acid chloride was azeotroped with 4×25 ml of chloroform to remove the excess oxalyl chloride. The acid chloride product was dissolved in 100 ml of chloroform, followed by the addition of 12.0 g (0.104 moles) of NHS and a slow addition of 11.48 g (0.113 mol) of TEA. The mixture was stirred at room temperature overnight. After washing the reaction mixture with 4×100 ml of water, the chloroform solution was dried over sodium sulfate. Removal of solvent gave 24.0 g of product for an 82% yield. Analysis on an NMR spectrometer was consistent with the desired product and it was used without further purification.

B. Synthesis of a Photoreactive Polyacrylamide Containing Hydrazide Ligands (Hydrazide Polymer).

Acrylamide, 8.339 g (0.117 mol), was dissolved in 112 ml of THF, followed by 0.241 g (1.50 mmol) of AIBN, 0.112 ml (0.74 mmol) of TEMED, 1.284 g (3.70 mmol) of BBA-APMA (prepared as described herein), and 0.377 g (1.2 mmol) of N-succinimidyl 6-maleimidohexanoate (prepared as described herein). The solution was deoxygenated with a helium sparge for 4 minutes, followed by an argon sparge for 4 minutes. The sealed vessel was then heated overnight at 55° C. to complete the polymerization. The precipitated polymer was isolated by filtration and was washed by stirring for 30 minutes with 100 ml of THF. The final product was recovered by filtration and dried in a vacuum oven to provide 9.64 g of solid, a 96% yield.

The above polymer (1.0 g) was dissolved in 50 ml of 0.05 M phosphate buffer at pH 8 and this solution was added to a second solution containing 0.696 g (5.89 mmol) of oxalic dihydrazide in 50 ml of 0.05 M phosphate buffer at pH 8. The combined solutions were stirred overnight at room temperature. The product was put into dialysis against deionized water using 6000–8000 molecular weight cutoff dialysis tubing. After six changes of water over two days, the polymer was isolated by lyophilization to give 850 mg of product. An analysis for hydrazide groups on this polymer gave a value of 0.0656 mmol of $NH_2$/g of polymer, 55% of theory.

C. Synthesis of a Photoreactive Polyacrylamide Containing Heparin Ligands (Heparin Polymer).

It is known that a controlled periodate oxidation of the uronic acid residues present in heparin will generate aldehyde functional groups, while retaining reasonable heparin activity. Unbleached heparin with an activity of 152 units/mg (from Celsus Laboratories, Cincinnati, Ohio) was dissolved at 250 mg/ml in 0.1 M acetate buffer (pH 5.5) and oxidized with sodium periodate at 20 mg/ml for 30 minutes to generate free aldehyde groups. Remaining periodate was inactivated by the addition of excess ethylene glycol. Then, the ethylene glycol and small molecular weight reaction products were removed by dialyzing overnight at 4° against 0.1 M acetate buffer (pH 5.5) using Spectra/Por 6,000 molecular weight cutoff dialysis tubing (from Spectrum Medical Industries). The oxidized heparin retained 95 units/mg of activity.

The concentration of oxidized heparin was adjusted to 15 mg/ml in 0.1 M acetate buffer (pH 5.5) and was reacted overnight with an equal volume of 20 mg/ml photopolyhydrazide in water at room temperature. The heparin polymer was used to coat biomaterials without further purification.

D. Immobilization of Heparin Polymer onto Regenerated Cellulose Membrane.

The heparin polymer was synthesized as described herein and immobilized onto regenerated cellulose (RC) membranes having a pore size of 0.45 mm. One inch diameter RC membranes were incubated with heparin polymer for 15 minutes, air dried and then illuminated for 45 seconds on each side. The discs were washed first in 10× PBS and then in PBS to remove unbound heparin polymer.

E. Evaluation of Thrombin Inhibition by Heparin Coated Membranes.

The antithrombotic activity of heparin is due to its inhibition of thrombin, which is a protease that is known to participate in the clotting cascade. Heparin inhibits thrombin activity by first binding to antithrombin III (ATIII). Then the heparin/ATIII complex binds to and inactivates thrombin, after which the heparin is released and can bind to another ATIII. The assay for inhibition of thrombin by immobilized heparin was conducted by measuring the cleavage of a chromogenic peptide substrate by thrombin and used previously described methods.

Each assay was conducted in 1 ml of PBS which contained 0.85 mg BSA (Sigma Chemical Co.), 10 mU human thrombin (Sigma Chemical Co.), 100 mU/ml ATIII (Baxter Biotech, Chicago, Ill.), and 0.17 μmole of the chromogenic thrombin substrate S-2238 (Kabi Pharmacia, Franklin, Ohio). To this assay solution was added either uncoated or heparin coated membranes (to evaluate heparin activity on the membranes) or standard concentrations of heparin (to generate standard curves of heparin content versus absorbance). The amounts of heparin that were added ranged from 2.5 to 25 mU. The color generated, measured as absorbance at 405 nm, by thrombin mediated cleavage of the S-2238 was read using a spectrophotometer after 2 hours of incubation at 37° C. The absorbance was directly related to the activity of the thrombin and, thus, inversely related to the amount of activation of ATIII induced by the heparin in solution or immobilized on the surface of the substrate. Activity of surface bound heparin was calculated by comparing the absorbance values generated with the membranes to the absorbance values generated with known amounts of added heparin.

This assay was then used to evaluate the heparin activity present on the coated and uncoated RC membranes. The coated membrane had heparin activity of 255 mU/sq.cm. whereas the uncoated had <0.1 mU/sq. cm.

Example 4

Lysine Polymers

A. Synthesis of N-α-[6-(maleimido)hexanoyl]lysine.

6-Maleimidohexanoic acid, 2.24 g (10.6 mmol) (prepared as described in Example 1) was dissolved in 10.76 g (84.8 mmol) of oxalyl chloride and stirred as a neat solution for 4 hours at room temperature. The excess oxalyl chloride was then removed under reduced pressure and the resulting acid chloride was dissolved in 25 ml of methylene chloride. This solution was added with stirring to a solution of 3.60 g (10.6 mmol) N-ε-t-BOC lysine t-butyl ester hydrochloride (Bachem California) in 25 ml of methylene chloride and 3.21 g (31.7 mmol) of TEA. The resulting mixture was stirred overnight under nitrogen. After this time, the mixture was treated with water and the organic layer was separated and dried over sodium sulfate. The solvent was removed and the product was purified on a silica gel flash chromatography column using a 0–5% methanol in chloroform solvent gradient. Pooling of the desired fractions and evaporation of solvent gave 5.20 g of product (98% yield). Analysis on an NMR spectrometer was consistent with the desired product.

The protected amino acid derivative, 0.566 g (1.14 mmol) was dissolved in 5 ml of trifluoroacetic acid with stirring. After stirring four hours at room temperature, the solvent was removed under reduced pressure. The resulting oil was tritruated with ether to remove residual trifluoroacetic acid to give 373 mg of product for a 98% yield. Analysis on an NMR spectrometer was consistent with the desired product.

B. Synthesis of a Photoreactive Polyacrylamide Containing ε-Amino Lysine Ligands (Lysine Polymer).

Acrylamide (0.22 g, 3.10 mmol), BBA-APMA (0.014 g, 0.039 mmol), and N-α-[6-(maleimido)hexanoyl]lysine (0.266 g, 0.784 mmol; prepared as described herein) were dissolved in 7.3 ml of dry DMSO. To initiate the polymerization, 8 mg (0.047 mmol) of AIBN and 4.0 μl of TEMED were added, followed by sparging with nitrogen to remove all oxygen. The mixture was then heated at 55° C. for 16 hours followed by evaporation of the DMSO under reduced pressure. The product was dissolved in DI water and dialyzed three days using 6–8K molecular weight cut off (MWCO) tubing against DI water. The resulting solution was lyophilized to give 160 mg of product.

C. Generation of Lysine Polymer Coatings on Polyurethane (PU).

PU sheets were cut into 1×1 cm pieces, washed with IPA and air dried. To improve wetting of the lysine polymer solution on PU, the PU pieces were treated with argon plasma at 250 watts, 0.25 torr, for 1 minute. The PU pieces were then immersed in an aqueous solution of lysine polymer (prepared as described herein, 1 mg/ml) for 5 minutes, air dried, and illuminated for 30 seconds. The samples were then washed overnight (in three changes of phosphate buffered saline, pH 7.4, which contained 1% Tween 20) to remove unbound lysine polymer. The coated PU pieces were stored in PBS containing 0.02% sodium azide until evaluated.

D. Quantitation of Lysine Polymer Coatings.

The lysine polymer (prepared as described above) was radiolabelled via reductive methylation and used to quantitate the levels immobilized onto polyurethane. The tritiated lysine polymer was coated onto PU pieces with or without illumination to determine the density of lysine polymer that was immobilized. After the wash procedure, samples were dissolved in Soluene-350 and counted in Hionic fluor (each from Packard Instrument Co., Meriden, Conn.). The table below shows the immobilized levels (±SEM) expressed in terms of μg/cm$^2$ and nmole/cm$^2$ of lysine moiety. Each level is the average of 4 replicates. The results show that 1.51 μg/cm$^2$ is immobilized after illumination, which is more than sufficient to produce a monolayer coating and is 3.8 times as much polymer as was retained with the adsorbed control.

| Treatment | Lysine polymer level (μg/cm$^2$) | Lysine moiety level (nmole/cm$^2$) |
| --- | --- | --- |
| Adsorbed | 0.40 ± 0.03 | 0.359 ± 0.027 |
| Illuminated | 1.51 ± 0.23 | 1.36 ± 0.21 |

E. Evaluation of Plasminogen Binding by Lysine Coated Polyurethane.

Others have described the covalent coupling of lysine to silane derivatized glass and the resultant lysine derivatized glass was reported to promote plasminogen binding, with the bound lysine exhibiting significant proteolytic activity. Such a surface is expected to demonstrate improved resistance to thrombus formation when placed in contact with blood. The coating chemistry used in the previous study utilized a short spacer and was limited to glass as a surface, whereas the photoreactive lysine polymer can be applied at high densities to a large range of biomaterials.

The lysine moiety in the lysine polymer is coupled via the α-amino group to the polymer backbone, and the ε-amino group is free to bind plasminogen. Therefore PU that is coated with the lysine polymer is expected to inhibit thrombus formation by reversibly binding plasminogen from blood, with the bound plasmin demonstrating proteolytic activity that cleaves fibrin and prevents fibrin clot formation on the coated surface.

Example 5

Prostaglandin Polymers

A. Synthesis of a Photoreactive Polyacrylamide Containing Primary Amine Ligands (Amine Polymer)

A solution of acrylamide (7.46 g, 105.1 mmoles), APMA-HCl (2.14 g, 11.9 mmoles), and BBA-APMA (0.837 g, 2.39 mmoles) is prepared in 170 ml of DMSO. To this solution is added AIBN (0.246 g, 1.50 mmoles) and TEMED (0.131 g, 1.13 mmoles). The solution is then deoxygenated by sparging with helium gas for a period of 10 minutes and is sealed and placed in a 55° C. oven for 18 hours to complete the polymerization. The polymer solution is diluted with water and dialyzed against deionized water using 12,000–14,000 MWCO dialysis tubing to remove solvent, unreacted monomers, and low molecular weight oligomers. The final product is isolated by lyophilization, and the photogroup load is determined by UV absorbance at 265 nm. The amine content of the polymer is determined using a trinitrobenzenesulfonate (TNBS) method. The photogroup and amine load can be changed by adjusting the quantity of monomers used in the polymerization.

B. Synthesis of a Photoreactive Polyacrylamide Containing Prostaglandin $E_1$ Ligands (Prostaglandin $E_1$ Polymer).

A solution of prostaglandin $E_1$ (Sigma Chemical Co.) (30 mg, 0.0846 mmole) in 5 ml of dry 1,4-dioxane is prepared, and NHS (10.7 mg, 0.0931 mmole) and DCC (26.2 mg, 0.127 mmole) are added to the solution. The mixture is stirred overnight at room temperature with formation of the 1,3-dicyclohexylurea (DCU) byproduct. The solid is removed by filtration, and the filter cake is rinsed with 1,4-dioxane. The solvent is removed under reduced pressure, and the resulting product is stored under dry conditions and used without further purification.

The amine polymer (synthesized as described above) is dissolved in DMSO at a concentration of 10 mg/ml, followed by the addition of 1.5 equivalents of the NOS-derivatized prostaglandin $E_1$ relative to the amine content of the amine polymer solution. Five equivalents of triethylamine are added to help catalyze the reaction. After an overnight reaction, the polymer solution is placed in dialysis against deionized water using 12,000–14,000 MWCO dialysis tubing to remove excess low molecular weight reactants. The product is isolated by lyophilization.

C. Synthesis of a Photoreactive Polyacrylamide Containing Carbacyclin Ligands (Carbacyclin Polymer).

A solution of carbacyclin (Sigma Chemical Co.) (5 mg, 0.0143 mmole) in 2 ml of dry 1,4-dioxane is prepared, and NHS (1.8 mg, 0.0157 mmole) and DCC (4.4 mg, 0.0215 mmole) are added to the solution. The mixture is stirred overnight at room temperature with formation of the DCU byproduct. The solid is removed by filtration, and the filter cake is rinsed with 1,4-dioxane. The solvent is removed under reduced pressure, and the resulting product is stored under dry conditions and used without further purification.

The amine polymer (synthesized as described above) is dissolved in DMSO at a concentration of 10 mg/ml, followed by the addition of 1.5 equivalents of the NOS-derivatized carbacyclin relative to the amine content of the amine polymer solution. Five equivalents of TEA are added to help catalyze the reaction. After an overnight reaction, the polymer solution is placed in dialysis against deionized water using 12,000–14,000 MWCO dialysis tubing to remove excess low molecular weight reactants. The product is isolated by lyophilization.

D. Prostaglandin Polymer Coatings

Each prostaglandin polymer (synthesized as described above) is diluted to 5 mg/ml in 50% (v/v) IPA in water and added to biomaterial samples (polyurethane, silicone rubber and polyethylene). The volume of prostaglandin containing polymer solution that is added to each polymer is just sufficient to cover the surface of each biomaterial (about 100 ml/cm$^2$). The polymer solution is allowed to dry onto each sample, after which each sample is illuminated for 1–2 minutes.

Both prostaglandin $E_1$ and carbacyclin (which is a stable analog of prostaglandin $I_2$; $PGI_2$) are known to inhibit platelet activation and thrombus formation. Therefore the prostaglandin coatings generated are expected to inhibit platelet activation and thrombus formation on biomaterials.

Example 6

Protein A Polymer

A. Synthesis of N-Succinimidyl 6-Methacrylamidohexanoate (MAm-EAC-NOS)

The ε-aminocaproic acid (EAC), 2.00 g (15.25 mmol), was added to a dry round bottom flask, followed by the addition of 2.58 g (16.73 mmol) of methacrylic anhydride. The resulting mixture was stirred at room temperature for two hours, followed by trituration with hexane. The hexane was decanted and the product was triturated two additional times to give 3.03 g of the acylated product (yield >99%). Without further purification, the product was dissolved in 50 ml of chloroform, followed by the addition of 1.922 g (16.7 mmol) of NHS and 6.26 g (30.3 mmol) of DCC. The mixture was stirred overnight at room temperature with protection from moisture. The resulting solid was removed by filtration and the filter cake was rinsed with chloroform. The solvent was removed under reduced pressure with 5 ppm of the monomethyl ether of hydroquinone (MEHQ) to prevent polymerization. The residue, 4.50 g, was redissolved in 45 ml of dry THF and the solution was used without further purification.

B. Synthesis of a Photoreactive Polyacrylamide Containing Protein A Ligands (Protein A Polymer).

To prepare the latent reactive NOS polymer, acrylamide (1.0 gm, 14.1 mmole) was dissolved in 15 ml of dry THF. To that solution was added 44 mg (0.149 mmole) of MAm-EAC-NOS (synthesized as described herein) and 158 mg (0.45 mmole) of BBA-APMA (synthesized as described in Example 1). For the initiator, 500 mg (3.04 mmole) of AIBN was added, followed by the addition of 50 μl of TEMED. The solution was bubbled with nitrogen and incubated at 55° C. for 18 hours to allow polymerization. The insoluble polymer was collected by filtration, and then dissolved in dry DMSO. The polymer was precipitated by being added dropwise to stirred ethanol, and was then collected by filtration and dried for storage until used. The product yield was 0.906 gm.

To couple protein A to the latent reactive NOS polymer, recombinant staphylococcal protein A (from Calbiochem-Novabiochem Corp., San Diego, Calif.) was dissolved at 10 mg/ml in 0.1 M carbonate buffer, pH 9. The latent reactive NOS polymer was dissolved at 100 mg/ml in 50 mM phosphate buffer, pH 6.8. Then 200 μl (20 mg) of the NOS polymer was added to 1 ml (10 mg) of the protein A solution, and the mixture was incubated overnight at 4° C. Evaluation by standard sodium dodecyl sulfate polyacrylamide gel electrophoresis (SDS-PAGE) revealed that more than 80% of the added protein A was incorporated into the resultant protein A polymer. The protein A polymer solution was used to coat biomaterials without further purification.

C. Generation of Protein A Polymer Coatings on Biomaterials.

The protein A polymer was then photocoupled to two types of membranes, polysulfone (PSO) membranes with a pore size of 0.2 mm (HT-200 membranes from Gelman Sciences, Ann Arbor, Mich.) and regenerated cellulose (RC) membranes with a pore size of 0.45 mm (no. SM 18606, from Sartorius, Edgewood, N.Y.). Each membrane was in the form of a disc that was 1 inch in diameter. Prior to addition of the protein A polymer, each membrane was washed first in 1:1 (v/v) isopropanol:0.1 N HCl and then in water.

The protein A polymer (estimated concentration of 8.67 mg/ml) was then added to each type of membrane (1 ml of polymer per 4–6 discs) and incubated overnight at 4° C. Then the discs were removed from the polymer solution, air dried, and illuminated for 1 minute on each side in a controlled temperature chamber (at 10° C.). Illumination was produced with a Dymax lamp as described herein.

The membranes were then washed to remove unbound protein A polymer. The wash was achieved by placing the coated disks in membrane holders (MAC-25 holder, from Amicon, Beverly, Mass.), with 2–4 membranes being placed in each holder. The membranes were then sequentially washed with: 1) 10 ml of 0.1 M glycine in 2% acetic acid, 2) 10 ml of 10× PBS, and 3) 30 ml of PBS. The washed membranes were then stored in PBS containing 0.05% sodium azide until used.

D. Evaluation of Activity of Protein A Polymer Coatings on Biomaterials.

Protein A is a bacterial protein that binds specifically to the $F_c$ region of immunoglobulin G (IgG) molecules. The activity of the protein A coating on each type of membrane was evaluated by assaying for binding by added IgG. Uncoated membranes were used as controls. For this assay, 2 ml of rabbit serum was diluted 1:5 in PBS and perfused through the coated membranes at 2–3 ml/min. The membranes were then washed with PBS to remove unbound IgG. The bound IgG was then eluted with 0.1 M glycine in 2% acetic acid. The amount of eluted IgG was determined by measuring the absorbance of the eluant at 280 nm and using an extinction coefficient ($\epsilon_{280}$) of 1.4 ml/cm-mg to calculate the mg of eluted IgG. Also the IgG that eluted from each membrane type was evaluated for purity by reduced SDS PAGE analysis. With the biomaterials coated with protein A polymer, the eluted protein was greater than 90% light and heavy chains of IgG. In contrast, the major protein that eluted from uncoated controls was albumin.

Three discs of each type (PSO or RC) were placed in a MAC-25 holder and evaluated using this procedure. The table below shows the average amounts of IgG that eluted from each membrane type; with each value being the average of 10 determinations (10 cycles) for 3 PSO disks and the average of 3 determinations (3 cycles) for 3 RC disks.

| Membrane type | Coating | IgG eluted) (mg/disc) | Fold greater IgG on protein A coating |
|---|---|---|---|
| Polysulfone | uncoated control | 0.020 | |
| Polysulfone | protein A polymer | 0.680 | 34 |
| Regenerated cellulose | uncoated control | 0.006 | |
| Regenerated cellulose | protein A polymer | 0.383 | 64 |

These results show that each type of coated membrane binds 34–64 fold more IgG than does its respective uncoated control. Also, protein A in the polymer has a stable conformation and is tenaciously bound, since there is no decrease in IgG elution after 10 cycles of serum addition and IgG elution.

Example 7

IgG Polymers

A. Synthesis of a Photoreactive Polyacrylamide Containing N-Oxysuccinimide Ligands (NOS Polymer).

Acrylamide, 3.897 g (0.0548 mol), was dissolved in 53 ml of THF, followed by 0.115 g (0.70 mmol) of AIBN, 0.053 ml of TEMED, 0.204 g (0.58 mmol) of BBA-APMA (prepared as described in Example 1), and 0.899 g (2.9 mmol) of N-succinimidyl 6-maleimidohexanoate (prepared as described in Example 3). The solution was deoxygenated with a helium sparge for 4 minutes, followed by an argon sparge for 4 minutes. The sealed vessel was then heated overnight at 55° C. to complete the polymerization. The precipitated polymer was isolated by filtration and was washed by stirring for 30 minutes with 100 ml of THF. The final product was recovered by filtration and dried in a vacuum oven to provide 4.688 g of solid, a 94% yield.

B. Synthesis and Immobilization of a Photoreactive Polyacrylamide Containing IgG Ligands.

IgG molecules are a class of antibody molecules that bind to specific antigens. Triated rabbit anti-glucose oxidase IgG was used so that the tritium label could be used to quantitate the immobilized level of IgG and glucose oxidase binding could be evaluated to assay IgG activity. NOS polymer (50 mg) (prepared as described herein) was added to 100 mg of [$^3$H] IgG (in 100 ml of 0.1 M sodium carbonate at pH 9) and allowed to react overnight at 4° C. The IgG polymer was used without further purification.

Polyester membrane (Accuwick from Pall Corporation) was cut into 6 mm discs, and 4 μl aliquots of the IgG polymer were spotted on each of 19 discs. Three discs were left as controls that were neither illuminated or washed. Eight discs were illuminated for 1 minute and 8 discs were left nonilluminated. The latter 8 illuminated and 8 nonilluminated discs were washed with 25 mM bis(2-hydroxyethyl) iminotris(hydroxymethyl)methane (BIS-TRIS) at pH 7.2 containing 1% lactose, 1% BSA and 0.1% Brij 35.

To quantitate the immobilized levels of IgG polymer, the 3 control (uncoated, unwashed) discs and 3 each of the illuminated and nonilluminated conditions were dissolved in Soluene (0.5 ml) and counted in 5 mls of Hionic Fluor. The results are reported in the table below. A comparison of the illuminated (washed) to the control (uncoated, unwashed) shows that 75% of the added IgG polymer was retained after illumination. In contrast, with the nonilluminated samples, only 12.5% of the added IgG polymer was retained.

| Treatment | IgG Amount on discs (ug) | | | IgG Activity ($A_{655}$) | | |
|---|---|---|---|---|---|---|
| | n | mean | SEM | n | mean | SEM |
| Control (uncoated, unwashed) | 3 | 2.08 | 0.03 | 5 | not assayed | NA |
| Nonilluminated (washed) | 3 | 0.26 | 0.01 | 5 | 0.669 | 0.021 |
| Illuminated (washed) | 3 | 1.56 | 0.03 | 5 | 1.079 | 0.059 |

To quantitate the activity of the immobilized IgG, the remaining 5 illuminated and 5 nonilluminated discs were incubated with glucose oxidase at 0.1 mg/ml in PBS for 1 hour and washed 5 times with TNT (0.05 M Tris (hydroxymethyl)aminomethane, 0.15 M NaCl, 0.05% Tween-20). Each disc was then transferred to wells in a 96 well microtiter plate and assayed by adding 200 μl of 3,3',5,5'-tetramethylbenzidine (TMB) chromogen mixture (100 μl of TMB reagent from Kirkegaard & Perry Laboratories, Inc., 100 μl 0.2 M sodium phosphate pH 5.5, 10 mg of glucose and 4 μg of horseradish peroxidase) and allowing the color to develop for 20 minutes. Aliquots (100 μl) were then transferred to a separate microtiter plate and the absorbance was read at 655 nm. A comparison of the illuminated to nonilluminated samples shows that 61% greater activity was expressed by the illuminated samples.

Example 8

Streptavidin Polymer

A. Synthesis of a Photoreactive Polyacrylamide Containing Streptavidin Ligands

Streptavidin (from InFerGene Company, Benicia, Calif.) was coupled to the NOS polymer (prepared as described in Example 6). Streptavidin (15 mg) was dissolved in 1.5 ml of 0.1 M carbonate buffer (pH 9.0). The NOS polymer was prepared and dissolved in 5 mM acetate buffer (pH 5) to a final concentration of 100 mg/ml. The NOS polymer solution (0.3 ml) was added to the streptavidin solution (1.5 ml), and the mixture was stirred overnight at 4° C. The resulting streptavidin polymer was used without further purification or characterization.

B. Generation of Streptavidin Polymer Coatings on Surfaces

Solid glass rods (3 mm diameter×3 cm length) were washed by sonication in 1:1 (v/v) acetone in 0.1N HCl for 30 minutes, rinsed in water, acetone, dried at 100° C. for 1 hr., cooled, and stored desiccated until used. Bis (trimethoxysilylethyl)benzene (from United Chemical Technologies, Inc., Bristol, Pa.) was diluted to 10% (v/v) in acetone. The rods were dipped in the silane reagent for 30 seconds, air dried, dipped in water for 30 seconds, removed and cured at 100° C. for 15 minutes, and rinsed with acetone.

The organosilane primed glass rods were dipped into a solution of streptavidin polymer for 30 seconds. The glass rods were removed from the solution, allowed to air dry, and illuminated for 30 seconds with a Dymax lamp. Adsorption controls were prepared via the same protocol, except that they were not illuminated. Both type of coated rods were washed with PBS containing 0.05% Tween 20 to remove nonadherent streptavidin polymer.

C. Evaluation of Immobilized Streptavidin Polymer

Streptavidin is a receptor that binds strongly to biotin as its ligand. The activity of streptavidin polymer coating was evaluated by quantifying the binding of added biotin derivatized horseradish peroxidase (biotin-HRP, obtained from Pierce Chemical Company, Rockford, Ill.). The glass rods were incubated for one hour in a 9 μg/ml solution of biotin-HRP. The binding of underivatized HRP (added at 9 μg/mi) was evaluated as a control for nonspecific binding of HRP to the glass rods. The rods were then washed with PBS containing 0.05% Tween 20 to remove nonbound HRP, and the relative activity of bound HRP was evaluated with a TMB peroxidase substrate system (Kirkegaard and Perry Laboratory, Inc., Gaithersburg, Md.). HRP catalyzes the oxidation of TMB and produces a color that is quantitated spectrophotometrically at 405 nm. Each result is the average of 3 determinations.

| Coating on glass | Absorbance of Biotin-HRP | Absorbance of HRP |
|---|---|---|
| Uncoated control | 0.067 | 0.085 |
| Adsorbed streptavidin polymer | 0.285 | 0.065 |
| Covalent streptavidin polymer | 1.005 | 0.056 |

The results show the expected trends, with the greatest peroxidase activity being observed on rods that were coated with photoimmobilized streptavidin polymer (covalent streptavidin polymer) and to which had been added biotin-HRP. The adsorbed (nonilluminated) streptavidin polymer produced 3.5 fold less peroxidase activity, and the remaining variants which lacked streptavidin and/or biotin exhibited little peroxidase activity.

Example 9

Biotin Polymer

The photoreactive amine polymer (80 mg) (synthesized as described in Example 5) is dissolved in 2 ml of DMSO. To the polymer solution is added 40 mg of biotinamidocaproic acid 3-sulfo-N-hydroxysuccinimide ester (Sigma Chemical Co.) and 0.05 ml triethylamine. The solution is mixed for two hours at room temperature, then dialyzed against deionized water to remove any biotin that is not coupled to the polymer.

A solution of the biotin polymer (1.0 mg/ml in deionized water) is applied to wells of a polystyrene microtitration plate and incubated for one hour, after which the plate is illuminated for 1–2 minutes. The plate is then washed with deionized water to remove unbound biotin polymer.

Biotin is a ligand that binds to streptavidin as its receptor. Polystyrene microtitration plates are coated with biotin polymer and evaluated for activity by assaying the binding of streptavidin. A solution of straptavidin is added to the plates that are coated with biotin polymer and unbound streptavidin is removed by washing with deionized water. The retained streptavidin is quantitated by adding biotin-HRP and evaluating HRP activity.

Example 10

Magainin Polymer

A. Synthesis of Magainin Peptide Monomer

Magainin-2 was used in this example and was custom synthesized for BSI by Bachem, Inc. Torrance, Calif.) with a cysteine being added to the carboxyl terminus of the peptide. The resulting sequence of Magainin consisted of Gly Ile Gly Lys Phe Leu His Ser Ala Lys Lys Phe Gly Lys Ala Phe Val Gly Glu Ile Met Asn Ser Cys (Referred to herein as SEQ ID NO:14). As was described in Example 1, the underlined C (C) denotes a nonnative amino acid that was added to allow coupling via the sulfhydryl group.

Magainin (2.36 μmole) was dissolved in 0.5 ml of degassed water. To this solution was added 2.36 mole of Mal-MAm (dissolved in 20 μl chloroform) and 0.5 ml ethanol. The reaction was stirred for 90 minutes at room temperature, after which the solution was dried under nitrogen and resuspended in 1 ml water. The recovered magainin monomer solution was determined to have 5.5 mg/ml of magainin moiety, as determined by the MicroBCA assay (kit from Pierce Chemical Company, Rockford, Ill.).

B. Synthesis of Photoreactive Polyacrylamide Containing Magainin Ligand (Magainin Polymers)

BBA-APMA was dissolved at a concentration of 10 mg/ml in DMSO, and acrylamide was dissolved at a concentration of 100 mg/ml in water. The magainin monomer (0.48 μmole in 220 μl water) was not purified after being synthesized (as described above). The appropriate molar amounts of BBA-APMA (0.25 μmol in 44 μl of THF) and acrylamide (6.9 μmol in 120 μl of water) were then added to the reaction vial. An additional 300 μl of THF was added, and the mixture was degassed by water aspiration for 15 minutes. Ammonium persulfate (6.8 μl of 10% stock solution in water) and TEMED (1.5 μl) were added to catalyze the polymerization. The mixture was degassed again and incubated overnight at room temperature in a sealed dessicator. The resultant magainin polymer was dialyzed against water (using Spectra/Por 50,000 MWCO dialysis tubing; from Spectrum, Houston, Tex.) at 4° C. to remove unincorporated reactants and then lyophilized. Of the 1.2 mg of magainin peptide that was used to synthesize the methacryloyl magainin, 0.35 mg was present in the solubilized magainin polymer.

C. Evaluation of Immobilized Magainin Polymer

Magainin is a cationic peptide antibiotic that was originally isolated from the skin of *Xenopus laevis*. It is active against a broad spectrum of pathogens and acts at the surface of the pathogens. The activity of the magainin polymer was evaluated by a standard solution assay, which determined the minimum inhibitory concentration (MIC) of magainin polymer that was required to prevent the growth of bacteria. The MIC of magainin polymer was 50 μg/ml for both *Escherichia coli* (ATCC No. 25922) and for *Staphylococcus epidermidis* (ATCC No. 12228), whereas native monomeric magainin (not incorporated into either a magainin monomer or the magainin polymer) had an MIC of 6.25–12.5 μg/ml for *E. coli* and 25 μg/ml for *S. epidermidis*.

The magainin polymer is diluted to 250 μg/ml in 50% (v/v) IPA in water and added to biomaterial samples (PU, SR and PE). The volume of magainin polymer solution that is added to each polymer is just sufficient to cover the surface of each biomaterial (about 100 μl/cm$^2$). The polymer solution is allowed to dry onto each sample, after which each sample is illuminated for 1–2 minutes. The coated samples are washed in 0.1 N HCl followed by PBS.

The antimicrobial activity of immobilized magainin polymer is evaluated with a centrifugation assay. Sheets of biomaterials are cut into disks of 1.5 cm diameter, coated with magainin polymer, and placed in individual wells of 24-well culture plates. Bacteria (*E. coli* and *S. epidermidis*) are suspended at 200–400 colony forming units per ml (cfu/ml) in PBS. One ml aliquots of bacterial suspensions are placed in wells that contain magainin-coated biomaterials, and the plates are centrifuged at 3500×g at 4° C. for 20 minutes to sediment the bacteria on the coated biomaterial disks. The disks are then placed in tryptic soy agar (TSA) bacterial culture plates and overlaid with a thin layer of TSA. After overnight incubation at 37° C., the colonies of bacteria growing on the disks are counted. The magainin polymer coatings are expected to inhibit bacterial growth and support the growth of fewer colonies of bacteria than uncoated controls.

Example 11

β-Galactosidase Polymer

A. Synthesis of a Photoreactive Polyacrylamide Containing β-Galactosidase (β-Galactosidase Polymer)

A mixture containing 50 mg/ml of the NOS polymer (prepared as described in Example 6) and 6.4 mg/ml β-galactosidase (from Boehringer Mannheim, Indianapolis, Ind.) in 0.1 M sodium carbonate, pH 9, was prepared. The mixture was allowed to react at room temperature for 1 hour and stored at 4° C. overnight. The resultant β-galactosidase polymer solution was used without purification for the generation of crosslinked films.

B. Generation of Crosslinked Films.

Films were cast by placing 40 ml aliquots of the β-galactosidase polymer solution (synthesized as described herein) on a Teflon block and allowing each aliquot to dry. The resulting films were illuminated for 0.5 or 4 minutes as described above.

C. Assay for Integrity of the Films.

The integrity of the films was assayed by determining whether they would retain their shape after being placed in a solution of PBS. Films illuminated for 0.5 min. dissolved upon exposure to saline; whereas films illuminated for 4 minutes retained their shape. These results are consistent with light activation of the BBA groups producing covalent crosslinking of invention polymer molecules.

The crosslinked β-galactosidase polymer was washed 3 times with 1 ml of PBS to remove nonincorporated enzyme. The last wash (0.2 ml) and the recovered film were each analyzed for enzyme activity using o-nitrophenol-β-D-galactopyranoside (o-NPG) (from Pierce, Rockford, Ill.) at 1 mg/ml in water using the protocol described in the "Worthington Enzyme Manual" (Worthington Biochemical Corp., Freehold, N.J., 1977). The last wash showed no β-galactosidase activity while the film gave the yellow nitrophenol product. This result demonstrated that the β-galactosidase moiety was active after the invention polymer was crosslinked to form an insoluble biomaterial.

Example 12

DNA Polymer

A model oligodeoxynucleotide (oligoDNA) probe with a sequence from exon 1 of the H-2K$^b$ gene of the major histocompatibility complex was synthesized and used as a capture probe. The sequence of the oligoDNA capture probe was 5'-GTCTGAGTCG GAGCCAGGGC GGCCGCCAAC AGCAGGAGCA (Referred to herein as SEQ ID NO:15)-3' and was synthesized with an aliphatic C12 spacer at the 5' end that terminated with a primary amine. The oligoDNA capture probe (80 μg, or 6 nmole) was coupled via the terminal amino group on the C12 spacer to 160 μg NOS polymer described herein in 50 mM phosphate buffer (pH 8.5, 1 mM EDTA, 0.24 ml final volume) at room temperature for 2.5 hours. The resultant DNA polymer was utilized without further purification of charaterization.

The DNA-polymer was applied to microplate wells (polypropylene plates from Corning Costar Corporation, Cambridge, Mass.) at 10 pmole (in 0.1 ml solution) per well and incubated for 10–30 minutes. The plates containing DNA polymer solutions were illuminated for 1.5 minutes with a Dymax lamp as described herein except that a filter was used that removes light of wavelengths shorter than 300 nm. A control consisted of oligoDNA capture probe (10 pmole in 0.1 ml 50 mM phosphate buffer, pH 8.5, 1 mM EDTA) that was added to wells, allowed to adsorb for 2.5 hr., and not illuminated. The plates were washed with phosphate buffered saline containing 0.05% Tween 20 in PBS to remove unbound DNA-polymer or control oligoDNA capture probe.

A detection probe with a sequence complementary to the capture probe described herein was synthesized with a biotin at the 5' end and used to evaluate the activity of the immobilized DNA polymer. The sequence of the detection probe was 5'-CCGTGCACGC TGCTCCTGCT GTTG-GCGGCC GCCCTGGCTC CGACTCAGAC (Referred to herein as SEQ ID NO:16)-3'. A control detection probe consisting of a noncomplementary sequence from exon 2 of the H-2K$^b$ gene was also synthesized with a biotin moiety at the 5' end.

The binding of each detection probe was assayed by subsequently adding a conjugate of streptavidin and horseradish peroxidase (SA-HRP, available from Pierce, Rockford, Ill.) and measuring the activity of the bound HRP. For this assay, the coated plates were blocked with hybridization buffer (0.75 M NaCl, 0.075 M citrate, pH 7.0, 0.1% lauroylsarcosine, 1% casein, and 0.02% sodium dodecyl sulfate) at 55° C. for 30 minutes. Complementary and noncomplementary detection probes were added at 50 fmole per 0.1 ml of hybridization buffer per well and incubated for one hour at 55° C. The plates were then washed with 0.3 M NaCl, 0.03 M citrate, pH 7.0 containing 0.1% SDS for 5 minutes at 55° C. SA-HRP was added at 0.5 µg/ml and incubated for 30 minutes at 37° C. The plates were then washed with 0.05% Tween 20 in PBS, followed by addition of peroxidase substrate (TMB Microwell Peroxidase substrate system from Kirkegarrd and Perry Laboratories, Gaithersburg, Md.) and measurement of absorbance at 655 nm on a microplate reader (model 3550, Bio-Rad Labs, Cambridge, Mass.). Since the polypropylene plates were opaque, the reacted substrate solutions were transferred to polystyrene plates to read the absorbance.

Hybridization Signals ($A_{655}$) from Polypropylene Microwells Coated with Photoimmobilized DNA-polymer or Adsorbed OligoDNA Capture Probe (n=3).

|  | Complementary detection probe | Noncomplementary detection probe |
| --- | --- | --- |
| Adsorbed oligo DNA capture probe | 0.037 ± 0.005 | 0.033 ± 0.001 |
| Photoimmobilized DNA polymer | 1.170 ± 0.079 | 0.068 ± 0.010 |

The results in the above table provide the hybridization signals from polypropylene microwells coated with photoimmobilized DNA-polymer or adsorbed oligoDNA capture probe (n=3). These results demonstrate that the photoimmobilized DNA polymer binds 32-fold more complementary detection probe than does the adsorbed control, and neither coating binds the noncomplementary probe.

What is claimed is:

1. A polybifunctional reagent comprising a plurality of molecules each comprising a polymeric backbone bearing
(a) a plurality of pendent latent reactive moieties capable of being activated by exposure to a suitable energy source, and
(b) two or more pendent bioactive groups capable of specific, noncovalent interactions with complementary groups, the reagent being capable, upon activation of the latent reactive moieties, of forming a crosslinked material or surface coating in order to promote the attraction of such complementary groups,
    wherein the polymeric backbone comprises a synthetic polymer or copolymer selected from the group consisting of acrylics, vinyls, nylons, polyurethanes, and polyethers, and biodegradable polymers selected from the group consisting of polylactic acid, polyglycolic acid, polydioxanones, polyanhydrides, and polyorthoesters, and
    wherein the pendent latent reactive moieties and pendent bioactive groups are each coupled to the backbone via covalent bonds resulting from thermochemical reactions, such that said latent reactive moieties and said bioactive groups are provided along the length of the polymeric backbone.

2. A polybifunctional reagent according to claim 1, wherein one or more of the latent reactive moieties comprise photoreactive moieties that can be activated to form intermolecular covalent bonds between the reagent molecule and a biomaterial surface in order to form a coating thereon.

3. A polybifunctional reagent according to claim 1, wherein one or more of the latent reactive moieties comprise photoreactive moieties that can be activated to form intermolecular covalent bonds between adjacent reagent molecules in order to form a bulk material.

4. A polybifunctional reagent according to claim 1, wherein the bioactive groups are each, independently, selected from the group consisting of proteins, peptides, amino acids, carbohydrates, and nucleic acids, each being capable of binding noncovalently to specific and complement portions of molecules or cells.

5. A polybifunctional reagent according to claim 1, wherein the bioactive groups are each, independently, selected from the group consisting of antithrombotic agents, cell attachment factors, receptors, ligands, growth factors, antibiotics, enzymes and nucleic acids.

6. A polybifunctional reagent according to claim 5, wherein the bioactive groups comprise antithrombotic agents selected from the group consisting of heparin, hirudin, lysine, prostaglandins, streptokinase, urokinase, and plasminogen activator.

7. A polybifunctional reagent according to claim 5, wherein the bioactive groups comprise cell attachment factors selected from the group consisting of surface adhesion molecules and cell-cell adhesion molecules.

8. A polybifunctional reagent according to claim 7 wherein the bioactive groups comprise surface adhesion molecules selected from the group consisting of laminin, fibronectin, collagen, vitronectin, tenascin, fibrinogen, thrombospondin, osteopontin, von Willibrand Factor, and bone sialoprotein and active domains thereof.

9. A polybifunctional reagent according to claim 7 wherein the bioactive groups comprise cell-cell adhesion molecules selected from the group consisting of N-cadherin and P-cadherin and active domains thereof.

10. A polybifunctional reagent according to claim 5 wherein the bioactive group comprise growth factors selected from the group consisting of fibroblastic growth factors, epidermal growth factor, platelet-derived growth factors, transforming growth factors, vascular endothelial growth factor, bone morphogenic proteins and other bone growth factors, and neural growth factors.

11. A polybifunctional reagent according to claim 5 wherein the bioactive groups comprise a ligand or receptor selected from the group consisting of antibodies, antigens, avidin, streptavidin, biotin, heparin, type IV collagen, protein A, and protein G.

12. A polybifunctional reagent according to claim 5 wherein the bioactive groups comprise an antibiotic selected from the group consisting of antibiotic peptides.

13. A polybifunctional reagent according to claim 5 wherein the bioactive groups comprise enzymes.

14. A polybifunctional reagent according to claim 5 wherein the bioactive groups comprise nucleic acid sequences capable of selectively binding complementary nucleic acid sequences.

15. A polybifunctional reagent according to claim 5 wherein one or more of the latent reactive moieties comprise photoreactive moieties that each comprise a photoactivatable ketone.

16. A polybifunctional reagent according to claim 1 wherein the acrylic polymers and copolymers comprise base monomers selected from the group consisting of hydroxyethyl acrylate, hydroxyethyl methbacrylate, glyceryl acrylate, glyceryl methacrylate, acrylic acid, methacrylic acid, acrylamide, and methacrylamide; the vinyl polymers and copolymers comprise base monomers selected from the group consisting of vinyl pyrrolidone and vinyl alcohol; the nylon polymers and copolymers comprise base monomers selected from the group consisting of caprolactam, lauryl lactam, hexamethylene adipamide, and hexamethylene dodecanediamide; and the polyether polymers and copolymers comprise base monomers selected from the group consisting of ethylene oxide, propylene oxide, and butylene oxide.

17. A polybifunctional reagent according to claim 1 wherein the polymeric backbone of the reagent provides between about 40 and about 400 carbon atoms per photoreactive group, and between about 5 and about 200 carbon atoms per bioactive group, when the bioactive groups have a molecular weight of less than 3000, or between about 10 and about 5000 carbon atoms when the bioactive groups have a molecular weight of between 3,000 and about 50,000.

18. A polybifunctional reagent according to claim 1 wherein one or more of the latent reactive moieties comprise photoreactive groups independently selected from the group consisting of photoreactive aryl ketones, azides, diazo compounds, diazirines, and ketenes.

19. A polybifunctional reagent according to claim 18 wherein the aryl ketones are selected from acetophenone, benzophenone, anthraquinone, anthrone, and heterocyclic analogues of anthrone or their substituted derivatives.

20. A polybifunctional reagent according to claim 18 wherein the azides are selected from the group consisting of aryl azides, acyl azides, azido formates, sulfonyl azides, and phosphoryl azides.

21. A polybifunctional reagent according to claim 20 wherein the aryl azides are selected from phenyl azide and 4-fluoro-3-nitrophenyl azide, the acyl azides are selected from benzoyl azide and p-methylbenzoyl azide, the azido formates are selected from ethyl azidoformate and phenyl azidoformate., the sulfonyl azides comprise benzenesulfonyl azide, and the phosphoryl azides are selected from diphenyl phosphoryl azide and diethyl phosphoryl azide.

22. A polybifunctional reagent according to claim 18 wherein the diazo compounds are selected from diazoalkanes, diazoketones, diazoacetates, and beta-keto-alpha-diazoacetates.

23. A polybifunctional reagent according to claim 2 wherein the biomaterial surface is selected from synthetic polymers, natural materials, metals, ceramics, glass, silica and sapphire.

24. A polybifunctional reagent according to claim 23 wherein the synthetic polymers are selected from oligomers, homopolymers, and copolymers resulting from either addition or condensation polymerizations.

25. A polybifunctional reagent according to claim 24 wherein the polymers are selected from acrylics, vinyls, nylons, polyurethanes, polycarbonates, polyamides, polysulfones, poly(ethylene terephthalate), polylactic acid, polyglycolic acid, polydimethylsiloxanes, polyetheretherketone and polytetrafluoroethylene.

26. A polybifunctional reagent according to claim 25 wherein the acrylics are selected from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide.

27. A polybifunctional reagent according to claim 25 wherein the vinyls are selected from ethylene, propylene, styrene, vinyl chloride, vinyl acetate, vinyl pyrrolidone, and vinylidene difluoride.

28. A polybifunctional reagent according to claim 25 wherein the nylons are selected from polycaprolactam, polylauryl lactam, polyhexamethylene adipamide, and polyhexamethylene dodecanediamide.

29. A polybifunctional reagent according to claim 23 wherein the biomaterial surface comprises a natural material selected from human tissue and organic materials.

30. A polybifunctional reagent according to claim 29 wherein the human tissue is selected from bone, cartilage, skin and teeth and the organic materials are selected from wood, cellulose, compressed carbon and rubber.

31. A polybifunctional reagent according to claim 23 wherein the biomaterial surface does not itself possess abstractable hydrogens to which the photogroups can form covalent bonds, and instead the reagent is photochemically attached by applying a suitable primer coating which bonds to the biomaterial surface and provides a suitable substrate for binding by the photogroups.

32. A polybifunctional reagent according to claim 31 wherein the biomaterial surface is selected from metals and ceramics which have oxide groups on their surfaces and are made suitable for coupling via photochemistry by adding a primer coating that binds to the oxide groups and provides abstractable hydrogens.

33. A polybifunctional reagent according to claim 32 wherein the metals are selected from titanium, stainless steel, and cobalt chromium.

34. A polybifunctional reagent according to claim 32 wherein the ceramics are selected from silicon nitride, silicon carbide, zirconia, and alumina.

35. A polybifunctional reagent according to claim 31 wherein the primer coating comprises an organosilane reagent.

36. A polybifunctional reagent according to claim 31 wherein the biomaterial surface is selected from noble metals, and the primer coating comprising functional groups with high affinity to noble metals are used to apply organic monolayers onto the surface thereof.

37. A polybifunctional reagent according to claim 36 wherein the noble metals are selected from gold, silver, copper, and platinum and the functional groups are selected from —CN, —SH, and —NH$_2$ groups.

38. A polybifunctional reagent according to claim 31 wherein the biomaterial surface without abstractable hydrogens is fibrous or porous and the reagent is applied in a manner sufficient to form covalently crosslinked polymer networks that fill the pores or form films around individual fibers.

39. A polybifunctional reagent according to claim 2 wherein the biomaterial surface is provided by a device selected from the group consisting of vascular devices, orthopedic devices, dental devices, ophthalmic devices, catheters, breast implants, synthetic prostheses, artificial organs, dialysis tubing and membranes, blood oxygenator tubing and membranes, blood bags, sutures, membranes, cell culture devices, chromatographic support materials, biosensors, diagnostic assay devices, enzyme reactors, affinity purification resins and membranes.

40. A polybifunctional reagent according to claim 39 wherein the vascular devices are selected from grafts, stents, shunts, valves, artificial hearts, and heart assist devices; the orthopedic devices are selected from joint implants, fracture repair devices, and artificial tendons; the dental devices are selected from dental implants and fracture repair devices; and the ophthalmic devices are selected from lenses and glaucoma drain shunts.

41. A polybifunctional reagent according to claim 2 wherein the reagent is coated on the biomaterial surface to provide an immobilized pattern of bioactive groups.

42. A polybifunctional reagent according to claim 2 wherein the reagent is coated on the biomaterial surface to provide an immobilized pattern of bioactive groups in the form of a microarray of specific binding molecules.

43. A polybifunctional reagent according to claim 42 wherein the bioactive groups are selected from antibodies, antigens, and nucleic acids.

44. A polybifunctional reagent according to claim 41 wherein the bioactive groups are immobilized on optical, electrochemical or semiconductor sensor surfaces to provide simultaneous multianalyte assay capabilities or multiple sensitivity range assays for single analytes.

45. A polybifunctional reagent according to claim 41 wherein the bioactive groups are immobilized by a patterned immobilization technique in which sequential processing/reaction steps occur along a fluid movement path in a multistep microvolume assay system.

46. A polybifunctional reagent according to claim 41 wherein the biomaterial surface is the surface of an electrode, and a coated pattern of cell attachment factors promote the attachment of neural cells to the electrode surface.

47. A polybifunctional reagent according to claim 41 wherein the bioactive groups are each, independently, selected from the group consisting of proteins, peptides, amino acids, carbohydrates, and nucleic acids, each being capable of binding noncovalently to specific and complementary portions of molecules or cells, and
wherein the acrylic polymers and copolymers comprise base monomers selected from the group consisting of hydroxyethyl acrylate, hydroxyethyl methacrylate, glyceryl acrylate, glyceryl methacrylate, acrylic acid, methacrylic acid, acrylamide, and methacrylamide; the vinyl polymers and copolymers comprise base monomers selected from the group consisting of vinyl pyrrolidone and vinyl alcohol; the nylon polymers and copolymers comprise base monomers selected from the group consisting of caprolactam, lauryl lactam, hexamethylene adipamide, and hexamethylene dodecanediamide; and the polyether polymers and copolymers comprise base monomers selected from the group consisting of ethylene oxide, propylene oxide, and butylene oxide, and
wherein one or more of the latent reactive moieties comprise photoreactive groups independently selected from the group consisting of photoreactive aryl ketones, azides, diazo compounds, diazirines, and ketenes.

48. A polybifunctional reagent according to claim 47 wherein the polymeric backbone of the reagent provides between about 40 and about 400 carbon atoms per photoreactive group, and between about 5 and about 200 carbon atoms per bioactive group, when the bioactive groups have a molecular weight of less than 3000, or between about 10 and about 5000 carbon atoms when the bioactive groups have a molecular weight of between 3,000 and about 50,000.

49. A polybifunctional reagent comprising a synthetic polymeric backbone bearing
    (a) a plurality of pendent photoreactive moieties in the form of photoactivatable ketones capable of being activated by exposure to a suitable energy source, and
    (b) two or more pendent bioactive groups capable of specific, noncovalent interactions with complementary groups and selected from the group consisting of proteins, peptides, amino acids, carbohydrates, and nucleic acids,
        wherein the polymeric backbone comprises a synthetic polymer or copolymer selected from the group consisting of acrylics, vinyls, nylons, polyurethanes, and polyethers, and biodegradable polymers selected from the group consisting of polylactic acid, polyglycolic acid, polydioxanones, polyanhydrides, and polyorthoesters, and
        wherein the pendent photoreactive moieties and pendent bioactive groups are each coupled to the backbone via covalent bonds resulting from thermochemical reactions, such that said photoreactive moieties and said bioactive groups are provided along the length of the polymeric backbone.

50. A reagent according to claim 49 wherein the acrylic polymers and copolymers comprise base monomers selected from the group consisting of hydroxyethyl acrylate, hydroxyethyl methacrylate, glyceryl acrylate, glyceryl methacrylate, acrylic acid, methacrylic acid, acrylamide, and methacrylamide, the vinyl polymers and copolymers comprise base monomers selected from the group consisting of vinyl pyrrolidone and vinyl alcohol; the nylon polymers and copolymers comprise base monomers selected from the group consisting of caprolactam, lauryl lactam, hexamethylene adipamide, and hexamethylene dodecanediamide; and the polyether polymers and copolymers comprise base monomers selected from the group consisting of ethylene oxide, propylene oxide, and butylene oxide.

51. A coated biomaterial surface, comprising the surface coated with the bound residues of an activated polybifunctional reagent comprising a polymeric backbone bearing
    (a) a plurality of pendent latent reactive moieties capable of being activated by exposure to a suitable energy source, and
    (b) two or more pendent bioactive groups capable of specific, noncovalent interactions with complementary groups,
        wherein the polymeric backbone comprises a synthetic polymer or copolymer selected from the group consisting of acrylics, vinyls, nylons, polyurethanes, and polyethers, and biodegradable polymers selected from the group consisting of polylactic acid, polyglycolic acid, polydioxanones, polyanhydrides, and polyorthoesters, and
        wherein the pendent latent reactive moieties and pendent bioactive groups are each coupled to the backbone via covalent bonds resulting from thermochemical reactions, such that said latent reactive moieties and said bioactive groups are provided along the length of the polymeric backbone.

52. A surface according to claim 51 wherein the acrylic polymers and copolymers comprise base monomers selected from the group consisting of hydroxyethyl acrylate, hydroxyethyl methacrylate, glyceryl acrylate, glyceryl methacrylate, acrylic acid, methacrylic acid, acrylamide, and methacrylamide; the vinyl polymers and copolymers comprise base monomers selected from the group consisting of vinyl pyrrolidone and vinyl alcohol; the nylon polymers and copolymers comprise base monomers selected from the group consisting of caprolactam, lauryl lactam, hexamethylene adipamide, and hexamethylene dodecanediamide; and of the polyether polymers and copolymers comprise base monomers selected from the group consisting of ethylene oxide, propylene oxide, and butylene oxide.

53. A surface according to claim 51 wherein the bioactive groups are each, independently, selected from the group consisting of proteins, peptides, amino acids, carbohydrates, and nucleic acids, each being capable of binding noncovalently to specific and complementary portions of molecules or cells.

54. A surface according to claim 51 wherein the bioactive groups are each, independently, selected from the group consisting of antithrombotic agents, cell attachment factors, receptors, ligands, growth factors, antibiotics, enzymes and nucleic acids.

55. A surface according to claim 54 wherein the bioactive groups comprise antithrombotic agents selected from the group consisting of heparin, hirudin, lysine, prostaglandins, streptokinase, urokinase, and plasminogen activator.

56. A surface according to claim 54 herein the bioactive groups comprise cell attachment factors selected from the group consisting of surface adhesion molecules and cell-cell adhesion molecules.

57. A surface according to claim 56 wherein the bioactive groups comprise surface adhesion molecules selected from the group consisting of laminin, fibronectin, collagen, vitronectin, tenascin, fibrinogen, thrombospondin, osteopontin, von Willibrand Factor, and bone sialoprotein and active domains thereof.

58. A surface according to claim 56 wherein the bioactive groups comprise cell-cell adhesion molecules selected from the group consisting of N-cadherin and P-cadherin and active domains thereof.

59. A surface according to claim 54 wherein the bioactive groups comprise growth factors selected from the group consisting of fibroblastic growth factors, epidermal growth factor, platelet-derived growth factors, transforming growth factors, vascular endothelial growth factor, bone morphogenic proteins and other bone growth factors, and neural growth factors.

60. A surface according to claim 54 wherein the bioactive groups comprise a ligand or receptor selected from the group consisting of antibodies, antigens, avidin, streptavidin, biotin, heparin, type IV collagen, protein A, and protein G.

61. A surface according to claim 54 wherein the bioactive groups comprise an antibiotic selected from the group consisting of antibiotic peptides.

62. A surface according to claim 54 wherein the bioactive groups comprise enzymes.

63. A surface according to claim 54 wherein the bioactive groups comprise nucleic acid sequences capable of selectively binding complementary nucleic acid sequences.

64. A surface according to claim 54 wherein one or more of the latent reactive moeities comprise photoreactive groups independently selected from the group consisting of photoreactive aryl ketones, azides, diazo compounds, diazirines, and ketenes.

65. A surface according to claim 64 wherein the aryl ketones are selected from acetophenone, benzophenone, anthraquinone, anthrone, and heterocyclic analogues of anthrone or their substituted derivatives.

66. A surface according to claim 64 wherein the azides are selected from the group consisting of aryl azides, acyl azides, azido formates, sulfonyl azides, and phosphoryl azides.

67. A surface according to claim 66 wherein the aryl azides are selected from phenyl azide and 4-fluoro-3-nitrophenyl azide, the acyl azides are selected from benzoyl azide and p-methylbenzoyl azide, the azido formates are selected from ethyl azidoformate and phenyl azidoformate., the sulfonyl azides comprise benzenesulfonyl azide, and the phosphoryl azides are selected from diphenyl phosphoryl azide and diethyl phosphoryl azide.

68. A surface according to claim 64 wherein the diazo compounds are selected from diazoalkanes, diazoketones, diazoacetates, and beta-keto-alpha-diazoacetates.

69. A surface according to claim 51 wherein the biomaterial surface is selected from synthetic polymers, natural materials, metals, ceramics, glass, silica and sapphire.

70. A surface according to claim 69 wherein the synthetic polymers are selected from oligomers, homopolymers, and copolymers resulting from either addition or condensation polymerizations.

71. A surface according to claim 70 wherein the polymers are selected from acrylics, vinyls, nylons, polyurethanes, polycarbonates, polyamides, polysulfones, poly(ethylene terephthalate), polylactic acid, polyglycolic acid, polydimethylsiloxanes, polyetheretherketone and polytetrafluoroethylene.

72. A surface according to claim 71 wherein the acrylics are selected from methyl crylate, methyl methacrylate, hydroxyethyl methacrylate, hydroxyethyl acrylate, acrylic acid, methacrylic acid, glyceryl acrylate, glyceryl methacrylate, methacrylamide, and acrylamide.

73. A surface according to claim 71 wherein the vinyls are selected from ethylene, propylene, styrene, vinyl chloride, vinyl acetate, vinyl pyrrolidone, and vinylidene difluoride.

74. A surface according to claim 71 wherein the nylons are selected from polycaprolactam, polylauryl lactam, polyhexamethylene adipamide, and polyhexamethylene dodecanediamide.

75. A surface according to claim 69 wherein the biomaterial surface comprises a natural material selected from human tissue and organic materials.

76. A surface according to claim 75 wherein the human tissue is selected from bone, cartilage, skin and teeth and the organic materials are selected from wood, cellulose, compressed carbon and rubber.

77. A surface according to claim 69 wherein the biomaterial surface does not itself possess abstractable hydrogens to which the photogroups can form covalent bonds, and instead the reagent is photochemically attached by applying a suitable primer coating which bonds to the biomaterial surface and provides a suitable substrate for binding by the photogroups.

78. A surface according to claim 77 wherein the biomaterial surface is selected from metals and ceramics which have oxide groups on their surfaces and are made suitable for coupling via photochemistry by adding a primer coating that binds to the oxide groups and provides abstractable hydrogens.

79. A surface according to claim 78 wherein the metals are selected from titanium, stainless steel, and cobalt chromium.

80. A surface according to claim 78 wherein the ceramics are selected from silicon nitride, silicon carbide, zirconia, and alumina.

81. A surface according to claim 77 wherein the primer coating comprises an organosilane reagent.

82. A surface according to claim 77 wherein the biomaterial surface is selected from noble metals, and the primer coating comprising functional groups with high affinity to noble metals are used to apply organic monolayers onto the surface thereof.

83. A surface according to claim 82 wherein the noble metals are selected from gold, silver, copper, and platinum and the functional groups are selected from —CN, —SH, and —NH$_2$ groups.

84. A surface according to claim 77 wherein the biomaterial surface without abstractable hydrogens is fibrous or porous and the reagent is applied in a manner sufficient to form covalently crosslinked polymer networks that fill the pores or form films around individual fibers.

85. A surface according to claim 51 wherein the biomaterial surface is provided by a device selected from the group consisting of vascular devices, orthopedic devices, dental devices, ophthalmic devices, catheters, breast implants, synthetic prostheses, artificial organs, dialysis tubing and membranes, blood oxygenator tubing and membranes, blood bags, sutures, membranes, cell culture devices, chromatographic support materials, biosensors, diagnostic assay devices, enzyme reactors, affinity purification resins and membranes.

86. A surface according to claim 85 vascular devices are selected from grafts, stents, shunts, valves, artificial hearts, and heart assist devices; the orthopedic devices are selected from joint implants, fracture repair devices, and artificial tendons; the dental devices are selected from dental implants and fracture repair devices; and the ophthalmic devices are selected from lenses and glaucoma drain shunts.

87. A surface according to claim 51 wherein the reagent is coated on the biomaterial surface to provide an immobilized pattern of bioactive groups.

88. A surface according to claim 51 wherein the reagent is coated on the biomaterial surface to provide an immobilized pattern of bioactive groups in the form of a microarray of specific binding molecules.

89. A surface according to claim 88 wherein the bioactive groups are selected from antibodies, antigens, and nucleic acids.

90. A surface according to claim 87 wherein the bioactive groups are immobilized on optical, electrochemical or semiconductor sensor surfaces to provide simultaneous multianalyte assay capabilities or multiple sensitivity range assays for single analytes.

91. A surface according to claim 87 wherein the bioactive groups are immobilized by a patterned immobilization technique in which sequential processing/reaction steps occur along a fluid movement path in a multistep microvolume assay system.

92. A surface according to claim 87 wherein the biomaterial surface is the surface of an electrode, and a coated pattern of cell attachment factors promote the attachment of neural cells to the electrode surface.

93. A surface according to claim 87 wherein the bioactive groups are each, independently, selected from the group consisting of proteins, peptides, amino acids, carbohydrates, and nucleic acids, each being capable of binding noncovalently to specific and complementary portions of molecules or cells, and wherein the acrylic polymers and copolymers comprise base monomers selected from the group consisting of hydroxyethyl acrylate, hydroxyethyl methacrylate, glyceryl acrylate, glyceryl methacrylate, acrylic acid, methacrylic acid, acrylamide, and methacrylamide; the vinyl polymers and copolymers comprise base monomers selected from the group consisting of vinyl pyrrolidone and vinyl alcohol; the nylon polymers and copolymers comprise base monomers selected from the group consisting of caprolactam, lauryl lactam, hexamethylene adipamide, and hexamethylene dodecanediamide; and the polyether polymers and copolymers comprise base monomers selected from the group consisting of ethylene oxide, propylene oxide, and butylene oxide, and wherein one or more of the latent reactive moieties comprise photoreactive groups independently selected from the group consisting of photoreactive aryl ketones, azides, diazo compounds, diazirines, and ketenes.

94. A surface according to claim 93 wherein the polymeric backbone of the reagent provides between about 40 and about 400 carbon atoms per photoreactive group, and between about 5 and about 200 carbon atoms per bioactive group, when the bioactive groups have a molecular weight of less than 3000, or between about 10 and about 5000 carbon atoms when the bioactive groups have a molecular weight of between 3,000 and about 50,000.

95. A crosslinked material comprising the bound residues of an activated polybifunctional reagent that initially comprised a polymeric backbone bearing (a) a plurality of pendent latent reactive moieties capable of being activated by exposure to a suitable energy source, and (b) two or more pendent bioactive groups capable of specific, noncovalent interactions with complementary groups, wherein the polymeric backbone comprises a synthetic polymer or copolymer selected from the group consisting of acrylics, vinyls, nylons, polyurethanes, and polyethers, and biodegradable polymers selected from the group consisting of polylactic acid, polyglycolic acid, polydioxanones, polyanhydrides, and polyorthoesters, and wherein the pendent latent reactive moieties and pendent bioactive groups are each coupled to the backbone via covalent bonds resulting from thermochemical reactions, such that said latent reactive moieties and said bioactive groups are provided along the length of the polymeric backbone.

96. A material according to claim 95 wherein the acrylic polymers and copolymers comprise base monomers selected from the group consisting of hydroxyethyl acrylate, hydroxyethyl methbacrylate, glyceryl acrylate, glyceryl methacrylate, acrylic acid, methacrylic acid, acrylamide, and methacrylamide; the vinyl polymers and copolymers comprise base monomers selected from the group consisting of vinyl pyrrolidone and vinyl alcohol; the nylon polymers and copolymers comprise base monomers selected from the group consisting of caprolactam, lauryl lactam, hexamethylene adipamide, and hexamethylene dodecanediamide; and the polyether polymers and copolymers comprise base monomers selected from the group consisting of ethylene oxide, propylene oxide, and butylene oxide.

97. A material according to claim 95, wherein the bioactive groups are each, independently, selected from the group consisting of proteins, peptides, amino acids, carbohydrates, and nucleic acids, each being capable of binding noncovalently to specific and complementary portions of molecules or cells.

98. A material according to claim 95, wherein the bioactive groups are each, independently, selected from the group consisting of antithrombotic agents, cell attachment factors, receptors, ligands, growth factors, antibiotics, enzymes and nucleic acids.

99. A material according to claim 98 wherein the bioactive groups comprise antithrombotic agents selected from the group consisting of heparin, hirudin, lysine, prostaglandins, streptokinase, urokinase, and plasminogen activator.

100. A material according to claim 98 wherein the bioactive groups comprise cell attachment factors selected from the group consisting of surface adhesion molecules and cell-cell adhesion molecules.

101. A material according to claim 100 wherein the bioactive groups comprise surface adhesion molecules selected from the group consisting of laminin, fibronectin, collagen, vitronectin, tenascin, fibrinogen, thrombospondin, osteopontin, von Willibrand Factor, and bone sialoprotein and active domains thereof.

102. A material according to claim 100 wherein the bioactive groups comprise cell-cell adhesion molecules selected from the group consisting of N-cadherin and P-cadherin and active domains thereof.

103. A material according to claim 98 wherein the bioactive groups comprise growth factors selected from the group consisting of fibroblastic growth factors, epidermal growth factor, platelet-derived growth factors, transforming growth factors, vascular endothelial growth factor, bone morphogenic proteins and other bone growth factors, and neural growth factors.

104. A material according to claim 98 wherein the bioactive groups comprise a ligand or receptor selected from the group consisting of antibodies, antigens, avidin, streptavidin, biotin, heparin, type IV collagen, protein A, and protein G.

105. A material according to claim 98 wherein the bioactive groups comprise an antibiotic selected from the group consisting of antibiotic peptides.

106. A material according to claim 98 wherein the bioactive groups comprise enzymes.

107. A material according to claim 98 wherein the bioactive groups comprise nucleic acid sequences capable of selectively binding complementary nucleic acid sequences.

108. A material according to claim 95 wherein one or more of the latent reactive moeities comprise photoreactive groups independently selected from the group consisting of photoreactive aryl ketones, azides, diazo compounds, diazirines, and ketenes.

109. A material according to claim 108 wherein the aryl ketones are selected from acetophenone, benzophenone, anthraquinone, anthrone, and heterocyclic analogues of anthrone or their substituted derivatives.

110. A material according to claim 108 wherein the azides are selected from the group consisting of aryl azides, acyl azides, azido formates, sulfonyl azides, and phosphoryl azides.

111. A material according to claim 110 wherein the aryl azides are selected from phenyl azide and 4-fluoro-3-nitrophenyl azide, the acyl azides are selected from benzoyl azide and p-methylbenzoyl azide, the azido formates are selected from ethyl azidoformate and phenyl azidoformate., the sulfonyl azides comprise benzenesulfonyl azide, and the phosphoryl azides are selected from diphenyl phosphoryl azide and diethyl phosphoryl azide.

112. A material according to claim 108 wherein the diazo compounds are selected from diazoalkanes, diazoketones, diazoacetates, and beta-keto-alpha-diazoacetates.

113. A method of coating a biomaterial surface, the method comprising the steps of
(a) providing on the surface a polybifunctional reagent comprising a polymeric backbone bearing
  (i) a plurality of pendent latent reactive moieties capable of being activated by exposure to a suitable energy source, and
  (ii) two or more pendent bioactive groups capable of specific, noncovalent interactions with complementary groups, and
(b) activating the latent reactive moieties in order to crosslink molecules of the polybifunctional reagent to themselves and/or to the surface,
wherein the polymeric backbone comprises a synthetic polymer or copolymer selected from the group consisting of acrylics, vinyls, nylons, polyurethanes, and polyethers, and biodegradable polymers selected from the group consisting of polylactic acid, polyglycolic acid, polydioxanones, polyanhydrides, and polyorthoesters, and
wherein the pendent latent reactive moieties and pendent bioactive groups are each coupled to the backbone via covalent bonds resulting from thermochemical reactions, such that said latent reactive moieties and said bioactive groups are provided alone the length of the polymeric backbone.

114. A method according to claim 113 wherein the acrylic polymers and copolymers comprise base monomers selected from the group consisting of hydroxyethyl acrylate, hydroxyethyl methacrylate, glyceryl acrylate, glyceryl methacrylate, acrylic acid, methacrylic acid, acrylamide, and methacrylamide; the vinyl polymers and copolymers comprise base monomers selected from the group consisting of vinyl pyrrolidone and vinyl alcohol; the nylon polymers and copolymers comprise base monomers selected from the group consisting of caprolactam, lauryl lactam, hexamethylene adipamide, and hexamethylene dodecanediamide; and the polyether polymers and copolymers comprise base monomers selected from the group consisting of ethylene oxide, propylene oxide, and butylene oxide.

115. A method according to claim 113 wherein the reagent is coated on the surface by spraying, dipping or brushing.

116. A method according to claim 113, wherein the bioactive groups are each, independently, selected from the group consisting of proteins, peptides, amino acids, carbohydrates, and nucleic acids, each being capable of binding noncovalently to specific and complementary portions of molecules or cells.

117. A method according to claim 113, wherein the bioactive groups are each, independently, selected from the group consisting of antithrombotic agents, cell attachment factors, receptors, ligands, growth factors, antibiotics, enzymes and nucleic acids.

118. A method according to claim 117 wherein the bioactive groups comprise antithrombotic agents selected from the group consisting of heparin, hirudin, lysine, prostaglandins, streptokinase, urokinase, and plasminogen activator.

119. A method according to claim 117 wherein the bioactive groups comprise cell attachment factors selected from the group consisting of surface adhesion molecules and cell-cell adhesion molecules.

120. A method according to claim 119 wherein the bioactive groups comprise surface adhesion molecules selected from the group consisting of laminin, fibronectin, collagen, vitronectin, tenascin, fibrinogen, thrombospondin, osteopontin, von Willibrand Factor, and bone sialoprotein and active domains thereof.

121. A method according to claim 119 wherein the bioactive groups comprise cell-cell adhesion molecules selected from the group consisting of N-cadherin and P-cadherin and active domains thereof.

122. A method according to claim 117 wherein the bioactive groups comprise growth factors selected from the group consisting of fibroblastic growth factors, epidermal growth factor, platelet-derived growth factors, transforming growth factors, vascular endothelial growth factor, bone morphogenic proteins and other bone growth factors, and neural growth factors.

123. A method according to claim 117 wherein the bioactive groups comprise a ligand or receptor selected from the group consisting of antibodies, antigens, avidin, streptavidin, biotin, heparin, type IV collagen, protein A, and protein G.

124. A method according to claim 117 wherein the bioactive groups comprise an antibiotic selected from the group consisting of antibiotic peptides.

125. A method according to claim 117 wherein the bioactive groups comprise enzymes.

126. A method according to claim 117 wherein the bioactive groups comprise nucleic acid sequences capable of selectively binding complementary nucleic acid sequences.

127. A method according to claim 113 wherein the one or more of the latent reactive moieties comprise photoreactive groups independently selected from the group consisting of photoreactive aryl ketones, azides, diazo compounds, diazirines, and ketenes.

128. A method according to claim 127 wherein the aryl ketones are selected from acetophenone, benzophenone, anthraquinone, anthrone, and heterocyclic analogues of anthrone or their substituted derivatives.

129. A method according to claim 127 wherein the azides are selected from the group consisting of aryl azides, acyl azides, azido formates, sulfonyl azides, and phosphoryl azides.

130. A method according to claim 129 wherein the aryl azides are selected from phenyl azide and 4-fluoro-3-nitrophenyl azide, the acyl azides are selected from benzoyl azide and p-methylbenzoyl azide, the azido formates are selected from ethyl azidoformate and phenyl azidoformate., the sulfonyl azides comprise benzenesulfonyl azide, and the phosphoryl azides are selected from diphenyl phosphoryl azide and diethyl phosphoryl azide.

131. A method according to claim 127 wherein the diazo compounds are selected from diazoalkanes, diazoketones, diazoacetates, and beta-keto-alpha-diazoacetates.

132. A method according to claim 113 wherein the biomaterial surface is selected from synthetic polymers, natural materials, metals, ceramics, glass, silica and sapphire.

133. A method according to claim 132 wherein the synthetic polymers are selected from oligomers, homopolymers, and copolymers resulting from either addition or condensation polymerizations.

134. A method according to claim 133 wherein the polymers are selected from acrylics, vinyls, nylons, polyurethanes, polycarbonates, polyamides, polysulfones, poly(ethylene terephthalate), polylactic acid, polyglycolic acid, polydimethylsiloxanes, polyetheretherketone and polytetrafluoroethylene.

135. A method according to claim 134 wherein the acrylics are selected from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide.

136. A method according to claim 134 wherein the vinyls are selected from ethylene, propylene, styrene, vinyl chloride, vinyl acetate, vinyl pyrrolidone, and vinylidene difluoride.

137. A method according to claim 134 wherein the nylons are selected from polycaprolactam, polylauryl lactam, polyhexamethylene adipamide, and polyhexamethylene dodecanediamide.

138. A method according to claim 132 wherein the biomaterial surface comprises a natural material selected from human tissue and organic materials.

139. A method according to claim 138 wherein the human tissue is selected from bone, cartilage, skin and teeth and the organic materials are selected from wood, cellulose, compressed carbon and rubber.

140. A method according to claim 132 wherein the biomaterial surface does not itself possess abstractable hydrogens to which the photogroups can form covalent bonds, and instead the reagent is photochemically attached by applying a suitable primer coating which bonds to the biomaterial surface and provides a suitable substrate for binding by the photogroups.

141. A method according to claim 140 wherein the biomaterial surface is selected from metals and ceramics which have oxide groups on their surfaces and are made suitable for coupling via photochemistry by adding a primer coating that binds to the oxide groups and provides abstractable hydrogens.

142. A method according to claim 141 wherein the metals are selected from titanium, stainless steel, and cobalt chromium.

143. A method according to claim 141 wherein the ceramics are selected from silicon nitride, silicon carbide, zirconia, and alumina.

144. A method according to claim 140 wherein the primer coating comprises an organosilane reagent.

145. A method according to claim 140 wherein the biomaterial surface is selected from noble metals, and the primer coating comprising functional groups with high affinity to noble metals are used to apply organic monolayers onto the surface thereof.

146. A method according to claim 145 wherein the noble metals are selected from gold, silver, copper, and platinum and the functional groups are selected from —CN, —SH, and —NH$_2$ groups.

147. A method according to claim 140 wherein the biomaterial surface without abstractable hydrogens is fibrous or porous and the reagent is applied in a manner sufficient to form covalently crosslinked polymer networks that fill the pores or form films around individual fibers.

148. A method according to claim 113 wherein the biomaterial surface is provided by a device selected from the group consisting of vascular devices, orthopedic devices, dental devices, ophthalmic devices, catheters, breast implants, synthetic prostheses, artificial organs, dialysis tubing and membranes, blood oxygenator tubing and membranes, blood bags, sutures, membranes, cell culture devices, chromatographic support materials, biosensors, diagnostic assay devices, enzyme reactors, affinity purification resins and membranes.

149. A method according to claim 148 wherein the vascular devices are selected from grafts, stents, shunts, valves, artificial hearts, heart assist devices; the orthopedic devices are selected from joint implants, fracture repair devices, and artificial tendons; the dental devices are selected from dental implants and fracture repair devices; and the ophthalmic devices are selected from lenses and glaucoma drain shunts.

150. A method according to claim 113 wherein the reagent is coated on the biomaterial surface to provide an immobilized pattern of bioactive groups.

151. A method according to claim 113 wherein the reagent is coated on the biomaterial surface to provide an immobilized pattern of bioactive groups in the form of a microarray of specific binding molecules.

152. A method according to claim 151 wherein the bioactive groups are selected from antibodies, antigens, and nucleic acids.

153. A method according to claim 150 wherein the bioactive groups are immobilized on optical, electrochemical or semiconductor sensor surfaces to provide simultaneous multianalyte assay capabilities or multiple sensitivity range assays for single analytes.

154. A method according to claim 150 wherein the bioactive groups are immobilized by a patterned immobilization technique in which sequential processing/reaction steps occur along a fluid movement path in a multistep microvolume assay system.

155. A method according to claim 150 wherein the biomaterial surface is the surface of an electrode, and a coated pattern of cell attachment factors promote the attachment of neural cells to the electrode surface.

156. A method according to claim 150 wherein the bioactive groups are each, independently, selected from the group consisting of proteins, peptides, amino acids, carbohydrates, and nucleic acids, each being capable of binding noncovalently to specific and complementary portions of molecules or cells, and
wherein the acrylic polymers and copolymers comprise base monomers selected from the group consisting of hydroxyethyl acrylate, hydroxyethyl methacrylate, glyceryl acrylate, glyceryl methacrylate, acrylic acid, methacrylic acid, acrylamide, and methacrylamide; the vinyl polymers and copolymers comprise base monomers selected from the group consisting of vinyl pyrrolidone and vinyl alcohol; the nylon polymers and copolymers comprise base monomers selected from the group consisting of caprolactam, lauryl lactam, hexamethylene adipamide, and hexamethylene dodecanediamide; and the polyether polymers and copolymers comprise base monomers selected from the group consisting of ethylene oxide, propylene oxide, and butylene oxide, and
wherein one or more of the latent reactive moieties comprise photoreactive groups independently selected from the group consisting of photoreactive aryl ketones, azides, diazo compounds, diazirines, and ketenes.

157. A method according to claim 156 wherein the polymeric backbone of the reagent provides between about 40 and about 400 carbon atoms per photoreactive group, and between about 5 and about 200 carbon atoms per bioactive group, when the bioactive groups have a molecular weight of less than 3000, or between about, 10 and about 5000 carbon atoms when the bioactive groups have a molecular weight of between 3,000 and about 50,000.

158. A method of coating a biomaterial surface, the method comprising the steps of
(a) providing a polybifunctional reagent comprising a polymeric backbone bearing
(i) a plurality of pendent latent reactive moieties capable of being activated by exposure to a suitable energy source, and
(ii) two or more pendent thermoreactive groups adapted to attach bioactive groups capable of specific, non-covalent interactions with complementary groups,
(b) contacting the surface with the reagent,
(c) activating the latent reactive moieties in order to crosslink molecules of the polybifunctional reagent to themselves and/or to the surface, and
(d) contacting thermoreactive groups of the reagent with the bioactive groups in order to covalently attach the bioactive groups to the reagent,
wherein the polymeric backbone comprises a synthetic polymer or copolymer selected from the group consisting of acrylics, vinyls, nylons, polyurethanes, and polyethers, and biodegradable polymers selected from the group consisting of polylactic acid, polyglycolic acid, polydioxanones, polyanhydrides, and polyorthoesters, and
wherein the pendent latent reactive moieties and pendent thermoreactive groups are each coupled to the backbone via covalent bonds resulting from thermochemical reactions, such that said latent reactive moieties and said thermoreactive groups are provided along the length of the polymeric backbone.

159. A method according to claim 158 wherein the acrylic polymers and copolymers comprise base monomers selected from the group consisting of hydroxyethyl acrylate, hydroxyethyl methacrylate, glyceryl acrylate, glyceryl methacrylate, acrylic acid, methacrylic acid, acrylamide, and methacrylamide; the vinyl polymers and copolymers comprise base monomers selected from the group consisting of vinyl pyrrolidone and vinyl alcohol; the nylon polymers and copolymers comprise base monomers selected from the group consisting of caprolactam, lauryl lactam, hexamethylene adipamide, and hexamnethylene dodecanediamide; and the polyether polymers and copolymers comprise base monomers selected from the group consisting of ethylene oxide, propylene oxide, and butylene oxide.

160. A method according to claim 158 wherein the reagent is coated on the surface by spraying, dipping or brushing.

161. A method according to claim 158, wherein the bioactive groups are each, independently, selected from the group consisting of proteins, peptides, amino acids, carbohydrates, and nucleic acids, each being capable of binding noncovalently to specific and complementary portions of molecules or cells.

162. A method according to claim 158, wherein the bioactive groups are each, independently, selected from the group consisting of antithrombotic agents, cell attachment factors, receptors, ligands, growth factors, antibiotics, enzymes and nucleic acids.

163. A method according to claim 162 wherein the bioactive groups comprise antithrombotic agents selected from the group consisting of heparin, hirudin, lysine, prostaglandins, streptokinase, urokinase, and plasminogen activator.

164. A method according to claim 162 wherein the bioactive groups comprise cell attachment factors selected from the group consisting of surface adhesion molecules and cell-cell adhesion molecules.

165. A method according to claim 164 wherein the bioactive groups comprise surface adhesion molecules selected from the group consisting of laminin, fibronectin, collagen, vitronectin, tenascin, fibrinogen, thrombospondin, osteopontin, von Willibrand Factor, and bone sialoprotein and active domains thereof.

166. A method according to claim 164 wherein the bioactive groups comprise cell-cell adhesion molecules selected from the group consisting of N-cadherin and P-cadherin and active domains thereof.

167. A method according to claim 162 wherein the bioactive groups comprise growth factors selected from the group consisting of fibroblastic growth factors, epidermal growth factor, platelet-derived growth factors, transforming growth factors, vascular endothelial growth factor, bone, morphogenic proteins and other bone growth factors, and neural growth factors.

168. A method according to claim 162 wherein the bioactive groups comprise a ligand or receptor selected from the group consisting of antibodies, antigens, avidin, streptavidin, biotin, heparin, type IV collagen, protein A, and protein G.

169. A method according to claim 162 wherein the bioactive groups comprise an antibiotic selected from the group consisting of antibiotic peptides.

170. A method according to claim 162 wherein the bioactive groups comprise enzymes.

171. A method according to claim 162 wherein the bioactive groups comprise nucleic acid sequences capable of selectively binding complementary nucleic acid sequences.

172. A method according to claim 158 wherein the latent reactive moieties comprise photoreactive groups and are each, independently, selected from the group consisting of photoreactive aryl ketones, azides, diazo compounds, diazirines, and ketenes.

173. A method according to claim 172 wherein the aryl ketones are selected from acetophenone, benzophenone, anthraquinone, anthrone, and heterocyclic analogues of anthrone or their substituted derivatives.

174. A method according to claim 172 wherein the azides are selected from the group consisting of aryl azides, acyl azides, azido formates, sulfonyl azides, and phosphoryl azides.

175. A method according to claim 174 wherein the aryl azides are selected from phenyl azide and 4-fluoro-3-nitrophenyl azide, the acyl azides are selected from benzoyl azide and p-methylbenzoyl azide, the azido formates are selected from ethyl azidoformate and phenyl azidoformate., the sulfonyl azides comprise benzenesulfonyl azide, and the phosphoryl azides are selected from diphenyl phosphoryl azide and diethyl phosphoryl azide.

176. A method according to claim 172 wherein the diazo compounds are selected from diazoalkanes, diazoketones, diazoacetates, and beta-keto-alpha-diazoacetates.

177. A method according to claim 158 wherein the biomaterial surface is selected from synthetic polymers, natural materials, metals, ceramics, glass, silica and sapphire.

178. A method according to claim 177 wherein the synthetic polymers are selected from oligomers, homopolymers, and copolymers resulting from either addition or condensation polymerizations.

179. A method according to claim 178 wherein the polymers are selected from acrylics, vinyls, nylons, polyurethanes, polycarbonates, polyamides, polysulfones, poly(ethylene terephthalate), polylactic acid, polyglycolic acid, polydimethylsiloxanes, polyetheretherketone and polytetrafluoroethylene.

180. A method according to claim 179 wherein the acrylics are selected from methyl acrylate, methyl methacrylate, hydroxyethyl methacrylate,hydroxyethyl acrylate, acrylic acid, methacrylic acid, glyceryl acrylate, glyceryl methacrylate, methacrylamide, and acrylamide.

181. A method according to claim 179 wherein the vinyls are selected from ethylene, propylene, styrene, vinyl chloride, vinyl acetate, vinyl pyrrolidone, and vinylidene difluoride.

182. A method according to claim 179 wherein the nylons are selected from polycaprolactam, polylauryl lactam, polyhexamethylene adipamide, and polyhexamethylene dodecanediamide.

183. A method according to claim 175 wherein the biomaterial surface comprises a natural material selected from human tissue and organic materials.

184. A method according to claim 183 wherein the human tissue is selected from bone, cartilage, skin and teeth and the organic materials are selected from wood, cellulose, compressed carbon and rubber.

185. A method according to claim 177 wherein the biomaterial surface does not itself possess abstractable hydrogens to which the photogroups can form covalent bonds, and instead the reagent is photochemically attached by applying a suitable primer coating which bonds to the biomaterial surface and provides a suitable substrate for binding by the photogroups.

186. A method according to claim 185 wherein the biomaterial surface is selected from metals and ceramics which have oxide groups on their surfaces and are made suitable for coupling via photochemistry by adding a primer coating that binds to the oxide groups and provides abstractable hydrogens.

187. A method according to claim 186 wherein the metals are selected from titanium, stainless steel, and cobalt chromium.

188. A method according to claim 186 wherein the ceramics are selected from silicon nitride, silicon carbide, zirconia, and alumina.

189. A method according to claim 185 wherein the primer coating comprises an organosilane reagent.

190. A method according to claim 185 wherein the biomaterial surface is selected from noble metals, and the primer coating comprising functional groups with high affinity to noble metals are used to apply organic monolayers onto the surface thereof.

191. A method according to claim 190 wherein the noble metals are selected from gold, silver, copper, and platinum and the functional groups are selected from —CN, —SH, and —NH$_2$ groups.

192. A method according to claim 185 wherein the biomaterial surface without abstractable hydrogens is fibrous or porous and the reagent is applied in a manner sufficient to form covalently crosslinked polymer networks that fill the pores or form films around individual fibers.

193. A method according to claim 158 wherein the biomaterial surface is provided by a device selected from the group consisting of vascular devices, orthopedic devices, dental devices, ophthalmic devices, catheters, breast implants, synthetic prostheses, artificial organs, dialysis tubing and membranes, blood oxygenator tubing and membranes, blood bags, sutures, membranes, cell culture devices, chromatographic support materials, biosensors, diagnostic assay devices, enzyme reactors, affinity purification resins and membranes.

194. A method according to claim 193 wherein the vascular devices are selected from grafts, stents, shunts, valves, artificial hearts, and heart assist devices; the orthopedic devices are selected from joint implants, fracture repair devices, and artificial tendons; the dental devices are selected from dental implants and fracture repair devices; and the ophthalmic devices are selected from lenses and glaucoma drain shunts.

195. A method according to claim 158 wherein the reagent is coated on the biomaterial surface to provide an immobilized pattern of bioactive groups.

196. A method according to claim 158 wherein the reagent is coated on the biomaterial surface to provide an immobilized pattern of bioactive groups in the form of a microarray of specific binding molecules.

197. A method according to claim 196 wherein the bioactive groups are selected from antibodies, antigens, and nucleic acids.

198. A method according to claim 195 wherein the bioactive groups are immobilized on optical, electrochemical or semiconductor sensor surfaces to provide simultaneous multianalyte assay capabilities or multiple sensitivity range assays for single analytes.

199. A method according to claim 195 wherein the bioactive groups are immobilized by a patterned immobilization technique in which sequential processing/reaction steps occur along a fluid movement path in a multistep microvolume assay system.

200. A method according to claim 195 wherein the biomaterial surface is the surface of an electrode, and a coated pattern of cell attachment factors promote the attachment of neural cells to the electrode surface.

201. A method according to claim 195 wherein the bioactive groups are each, independently, selected from the group consisting of proteins, peptides, amino acids, carbohydrates, and nucleic acids, each being capable of binding noncovalently to specific and complementary portions of molecules or cells, and wherein the acrylic polymers and copolymers comprise base monomers selected from the group consisting of hydroxyethyl acrylate, hydroxyethyl methacrylate, glyceryl acrylate, glyceryl methacrylate, acrylic acid, methacrylic acid, acrylamide, and methacrylamide; the vinyl polymers and copolymers comprise base monomers selected from the group consisting of vinyl pyrrolidone and vinyl alcohol; the nylon polymers and copolymers comprise base monomers selected from the group consisting of caprolactam, lauryl lactam, hexamethylene adipamide, and hexamethylene dodecanediamide; and the polyether polymers and copolymers comprise base monomers selected from the group consisting of ethylene oxide, propylene oxide, and butylene oxide, and wherein one or more of the latent reactive moieties comprise photoreactive groups independently selected from the group consisting of photoreactive aryl ketones, azides, diazo compounds, diazirines, and ketenes.

202. A method according to claim 201 wherein the polymeric backbone of the reagent provides between about 40 and about 400 carbon atoms per photoreactive group, and between about 5 and about 200 carbon atoms per bioactive group, when the bioactive groups have a molecular weight of less than 3000, or between about 10 and about 5000 carbon atoms when the bioactive groups have a molecular weight of between 3,000 and about 50,000.

203. A method for forming a crosslinked biomaterial, the method comprising the steps of
(a) providing a polybifunctional reagent comprising a polymeric backbone bearing
(i) a plurality of pendent latent reactive moieties capable of being activated by exposure to a suitable energy source, and
(ii) two or more pendent bioactive groups capable of specific, noncovalent interactions with complementary groups, and
b) activating the latent reactive moieties to form intermolecular covalent bonds between adjacent molecules of the polybifunctional reagent in order to form a crosslinked biomaterial,
wherein the polymeric backbone comprises a synthetic polymer or copolymer selected from the group consisting of acrylics, vinyls, nylons, polyurethanes, and polyethers, and biodegradable polymers selected from the group consisting of polylactic acid, polyglycolic acid, polydioxanones, polyanhydrides, and polyorthoesters, and
wherein the pendent latent reactive moieties and pendent bioactive groups are each coupled to the backbone via covalent bonds resulting from thermochemical reactions, such that said latent reactive moieties and said bioactive groups are provided along the length of the polymeric backbone.

204. A method according to claim 203 wherein the acrylic polymers and copolymers comprise base monomers selected from the group consisting of hydroxyethyl acrylate, hydroxyethyl methacrylate, glyceryl acrylate, glyceryl methacrylate, acrylic acid, methacrylic acid, acrylamide, and methacrylamide; the vinyl polymers and copolymers comprise base monomers selected from the group consisting of vinyl pyrrolidone and vinyl alcohol; the nylon polymers and copolymers comprise base monomers selected from the group consisting of caprolactam, lauryl lactam, hexamethylene adipamide, and hexamethylene dodecanediamide; and the polyether polymers and copolymers comprise base monomers selected from the group consisting of ethylene oxide, propylene oxide, and butylene oxide.

205. A method according to claim 203 wherein the bioactive groups are each, independently, selected from the group consisting of proteins, peptides, amino acids, carbohydrates, and nucleic acids, each being capable of binding noncovalently to specific and complementary portions of molecules or cells.

206. A method according to claim 203 wherein the bioactive groups are each, independently, selected from the group consisting of antithrombotic agents, cell attachment factors, receptors, ligands, growth factors, antibiotics, enzymes and nucleic acids.

207. A method according to claim 206 wherein the bioactive groups comprise antithrombotic agents selected from the group consisting of heparin, hirudin, lysine, prostaglandins, streptokinase, urokinase, and plasminogen activator.

208. A method according to claim 206 wherein the bioactive groups comprise cell attachment factors selected from the group consisting of surface adhesion molecules and cell-cell adhesion molecules.

209. A method according to claim 208 wherein the bioactive groups comprise surface adhesion molecules selected from the group consisting of laminin, fibronectin, collagen, vitronectin, tenascin, fibrinogen, thrombospondin, osteopontin, von Willibrand Factor, and bone sialoprotein and active domains thereof.

210. A method according to claim 208 wherein the bioactive groups comprise cell-cell adhesion molecules selected from the group consisting of N-cadherin and P-cadherin and active domains thereof.

211. A method according to claim 206 wherein the bioactive groups comprise growth factors selected from the group consisting of fibroblastic growth factors, epidermal growth factor, platelet-derived growth factors, transforming growth factors, vascular endothelial growth factor, bone morphogenic proteins and other bone growth factors, and neural growth factors.

212. A method according to claim 206 wherein the bioactive groups comprise a ligand or receptor selected, from the group consisting of antibodies, antigens, avidin, streptavidin, biotin, heparin, type IV collagen, protein A, and protein G.

213. A method according to claim 206 wherein the bioactive groups comprise an antibiotic selected from the group consisting of antibiotic peptides.

214. A method according to claim 206 wherein the bioactive groups comprise enzymes.

215. A method according to claim 206 wherein the bioactive groups comprise nucleic acid sequences capable of selectively binding complementary nucleic acid sequences.

216. A method according to claim 203 wherein the latent reactive moieties comprise photoreactive groups and are each, independently, selected from the group consisting of photoreactive aryl ketones, azides, diazo compounds, diazirines, and ketenes.

217. A method according to claim 216 wherein the aryl ketones are selected from acetophenone, benzophenone, anthraquinone, anthrone, and heterocyclic analogues of anthrone or their substituted derivatives.

218. A method according to claim 216 wherein the azides are selected from the group consisting of aryl azides, acyl azides, azido formates, sulfonyl azides, and phosphoryl azides.

219. A method according to claim 218 wherein the aryl azides are selected from phenyl azide and 4-fluoro-3-nitrophenyl azide, the acyl azides are selected from benzoyl azide and p-methylbenzoyl azide, the azido formates are selected from ethyl azidoformate and phenyl azidoformate., the sulfonyl azides comprise benzenesulfonyl azide, and the phosphoryl azides are selected from diphenyl phosphoryl azide and diethyl phosphoryl azide.

220. A method according to claim 216 wherein the diazo compounds are selected from diazoalkanes, diazoketones, diazoacetates, and beta-keto-alpha-diazoacetates.

* * * * *

UNITED STATES PATENT AND TRADEMARK OFFICE
CERTIFICATE OF CORRECTION

PATENT NO.       : 6,514,734 B1                                    Page 1 of 1
APPLICATION NO.  : 09/591564
DATED            : February 4, 2003
INVENTOR(S)      : Clapper et al.

It is certified that error appears in the above-identified patent and that said Letters Patent is hereby corrected as shown below:

Column 7, line 26, delete the "." after "reported".

Column 18, line 66, replace "C-aminocaproic" with --ε-aminocaproic--.

Signed and Sealed this

Second Day of January, 2007

JON W. DUDAS
*Director of the United States Patent and Trademark Office*